US008394261B2

(12) United States Patent
Litz et al.

(10) Patent No.: US 8,394,261 B2
(45) Date of Patent: *Mar. 12, 2013

(54) SULFOXIDATION CATALYSTS AND METHODS AND SYSTEMS OF USING SAME

(75) Inventors: Kyle E. Litz, Ballston Spa, NY (US); Tracey M. Jordan, Valley Falls, NY (US); Mark N. Rossetti, Castleton, NY (US); Anthony J. Loughran, Athens, NY (US); Jennifer L. Vreeland, Troy, NY (US)

(73) Assignee: Auterra, Inc., Malta, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/933,898

(22) PCT Filed: Oct. 31, 2008

(86) PCT No.: PCT/US2008/082095
§ 371 (c)(1),
(2), (4) Date: Sep. 22, 2010

(87) PCT Pub. No.: WO2009/120238
PCT Pub. Date: Oct. 1, 2009

(65) Prior Publication Data
US 2011/0011771 A1 Jan. 20, 2011

Related U.S. Application Data

(60) Provisional application No. 61/039,619, filed on Mar. 26, 2008.

(51) Int. Cl.
*C10G 25/00* (2006.01)

(52) U.S. Cl. .............. 208/189; 208/208 R; 208/240; 208/213; 208/190; 208/196

(58) Field of Classification Search .............. 208/208 R, 208/213, 240
See application file for complete search history.

(56) References Cited

U.S. PATENT DOCUMENTS

| 2,764,525 | A | | 9/1956 | Porter et al. |
|---|---|---|---|---|
| 2,910,434 | A | | 10/1959 | Hess et al. |
| 2,987,470 | A | | 6/1961 | Turken |
| 3,505,210 | A | | 4/1970 | Heimlich et al. |
| 3,565,793 | A | | 2/1971 | Herbstman et al. |
| 3,668,117 | A | | 6/1972 | Patel et al. |
| 3,819,509 | A | | 6/1974 | Wolk et al. |
| 3,945,914 | A | * | 3/1976 | Yoo et al. ............... 208/208 R |
| 3,964,995 | A | | 6/1976 | Wolk et al. |
| 4,192,736 | A | | 3/1980 | Kluksdahl |
| 4,374,949 | A | | 2/1983 | Massey et al. |
| 4,444,655 | A | | 4/1984 | Shiroto et al. |
| 4,645,589 | A | | 2/1987 | Krambeck et al. |
| 5,637,739 | A | | 6/1997 | Jacobsen et al. |
| 6,245,223 | B1 | | 6/2001 | Gorbaty et al. |
| 6,368,495 | B1 | | 4/2002 | Kocal et al. |
| 6,406,616 | B1 | | 6/2002 | Rappas et al. |
| 6,544,409 | B2 | | 4/2003 | De Souza |
| 6,673,236 | B2 | | 1/2004 | Stanciulescu et al. |
| 6,846,406 | B2 | | 1/2005 | Canos et al. |
| 7,144,499 | B2 | | 12/2006 | Han et al. |
| 7,153,414 | B2 | | 12/2006 | De Souza |
| 7,179,368 | B2 | | 2/2007 | Rabion et al. |
| 7,314,545 | B2 | | 1/2008 | Karas |
| 7,371,318 | B2 | | 5/2008 | Corma Canos et al. |
| 7,374,666 | B2 | | 5/2008 | Wachs |
| 7,790,021 | B2 | | 9/2010 | Kocal et al. |
| 7,875,185 | B2 | | 1/2011 | Zhang |
| 8,197,671 | B2 | | 6/2012 | Rankin et al. |
| 2002/0177522 | A1 | * | 11/2002 | Alexander et al. ............ 502/159 |
| 2002/0189975 | A1 | * | 12/2002 | De Souza .................. 208/208 R |
| 2004/0108252 | A1 | | 6/2004 | De Souza |
| 2004/0178121 | A1 | | 9/2004 | Leyshon et al. |
| 2004/0222134 | A1 | | 11/2004 | deSouza |
| 2004/0238410 | A1 | * | 12/2004 | Inoue et al. .................... 208/213 |
| 2006/0011510 | A1 | | 1/2006 | Toshima et al. |
| 2006/0180501 | A1 | * | 8/2006 | Da Silva et al. .......... 208/208 R |
| 2008/0308463 | A1 | | 12/2008 | Keckler et al. |
| 2009/0065399 | A1 | | 3/2009 | Kocal et al. |
| 2011/0031164 | A1 | | 2/2011 | Litz et al. |
| 2011/0108464 | A1 | | 5/2011 | Rankin et al. |

FOREIGN PATENT DOCUMENTS

WO 2009120238 A1 10/2009

OTHER PUBLICATIONS

Jain, Suman L., et al. Rehenium-Catalyzed Highly Efficient Oxidations of Tertiary Nitrogen Compounds to N-Oxides Using Sodium Percarbonate as Oxygen Source. Synlett, 2006, No. 16, pp. 2661-2663. Published on Web Sep. 22, 2006.
McKillop, Alexander, et al. Further Functional-Group Oxidations Using Sodium Perborate Tetrahedron, vol. 45, No. 11, pp. 3299 to 3306, 1989. Published in Great Britain.
Varma, Rajender S., et al. The Urea-Hydrogen Peroxide Complex: Solid-State Oxidative Protocols for Hydroxylated Aldehydes and Ketones (Dakin Reaction), Nitriles, Sulfides, and Nitrogen Heterocycles. Organic Letters, 1999, vol. 1, No. 2, pp. 189-191. Published on Web May 29, 1999.
Jana, Nirmal K., et al. Phase-Vanishing Methodology for Efficient Bromination, Alkylation, Epoxidation, and Oxidation Reactions of Organic Substrates. Organic Letters, 2003, vol. 5, No. 21, pp. 3787-3790. Published on Web Sep. 16, 2003.
Khodaei, Mohammad Mehdi, et al. H2O2/Tf2O System: An Efficient Oxidizing Reagent for Selective Oxidation of Sulfanes. Synthesis, 2008; No. 11, pp. 1682-1684. Published on Web Apr. 11, 2008.
Kim, Sung Soo, et al. A Mild and Highly Efficient Oxidation of Sulfide to Sulfoxides with Periodic Acid Catalyzed by FeCl3. Synthesis, 2002, No. 17, pp. 2484-2486. Published USA Feb. 12, 2002.
Qian, Weixing, et al. Efficient and Highly Selective Oxidation of Sulfides to Sulfoxides in the Presence of an Ionic Liquid Containing Hypervalent Iodine. Synlett, 2006, No. 5, pp. 709-712. Published on Web Mar. 9, 2006.
Matteucci, Mizio, et al. Mild and Highly Chemoselective Oxidation of Thioethers Mediated by Sc(OTf)3. Organic Letters, 2003, vol. 5, No. 3, 235-237. Published on Web Jan. 11, 2003.

(Continued)

Primary Examiner — Prem C Singh
Assistant Examiner — Michelle Stein
(74) Attorney, Agent, or Firm — Schmeiser, Olsen & Watts, LLP

(57) ABSTRACT

Catalysts amenable to oxidizing sulfur compounds and systems and methods of using these catalysts to effect the removal of sulfur from crude oil and crude oil distillates are disclosed. The catalyst is disposed with a titanyl moiety which serves to selectively coordinate sulfur compounds and affect their oxidation. The titanyl may be bound within a polymer or on the surface of a polymer or on the surface or in the pores of an inorganic support. The resulting oxidized sulfur compounds are readily separated from the initial crude oil or crude oil distillate streams by traditional separation techniques arrayed as described in the systems and methods disclosed.

10 Claims, 10 Drawing Sheets

OTHER PUBLICATIONS

Mba, Myriam, et al. C3-Symmetric Ti(IV) Triphenolate Amino Complexes as Sulfoxidation Catalysts with Aqueous Hydrogen Peroxide. Organic Letters, 2007, vol. 9, No. 1, pp. 21-24. Published on Web Dec. 9, 2006.

Drago, Carmelo, et al. Vanadium-Catalyzed Sulfur Oxidation/Kinetic Resolution in the Synthesis of Enantiomerically Pure Alkyl Aryl Sulfoxides. Agnew. Chem. Int. Ed, 2005, 44, pp. 7221-7223. Published on Web Oct. 17, 2005.

Egami, Hiromichi, et al. Fe(salan)-Catalyzed Asymmetric Oxidation of Sulfides with Hydrogen Peroxide in Water. J. Am. Chem. Soc., 2007, vol. 129, No. 29, pp. 8940-8941. Published on Web Jun. 29, 2007.

Sun, Jiangtao, et al. Efficient Asymmetric Oxidation of Sulfides and Kinetic Resolution of Sulfoxides Catalyzed by a Vanadium-Salan System. J. Org. Chem., 2004, vol. 69, No. 24, pp. 8500-8503. Published on Web Oct. 28, 2004.

Karimi, Babak, et al. Selective Oxidation of Sulfides to Sulfoxides Using 30% Hydrogen Peroxide Catalyzed with a Recoverable Silica-Based Tungstate Interphase Catalyst. Organic Letters, 2005, vol. 7, No. 4, pp. 625-628. Published on Web Jan. 25, 2005.

Ali, Mohammed Hashmat, et al. Ceric Ammonium Nitrate Catalyzed Oxidation of Sulfides to Sulfoxides. Synthesis, 2007, No. 22, pp. 3507-3511. Published on Web Oct. 16, 2007.

Imada, Yasushi, et al. Flavin Catalyzed Oxidations of Sulfides and Amines with Molecular Oxygen. J. Am Chem. Soc., 2003, vol. 125, No. 10, pp. 2868-2869. Published on Web Feb. 12, 2003.

Varma, Rajender S., et al. The Urea-Hydrogen Peroxide Complex: Solid-State Oxidatives Protocols for Hydroxylated Aldehydes and Ketones (Dakin Reaction), Nitriles, Sulfides, and Nitrogen Heterocycles. Organic Letters, 1999, vol. 1, No. 2, pp. 189-191. Published on Web May 29, 1999.

Jana, Nirmal K., et al. Phase-Vanishing Methodology for Efficient Bromination, Alkylation, Epoxidation, and Oxidation Reactions of Organic Substrates. Organic Letters, 2003, vol. 5, No. 21, pp. 3787-3790. Published on Web Sep. 16, 2003.

Shaabani, Ahmad, et al. Green oxidations. The use of potassium permanganate supported on manganese dioxide. Tetrahedron, 2004, 60, pp. 11415-11420. Published on Web Oct. 12, 2004.

Wozniak, Lucyna A., et al. Oxidation in Organophosphorus Chemistry: Potassium Peroxymonosulphate. Tetrahedron, 1999, 40, pp. 2637-2640. Received Oct. 13, 1998; Accepted Feb. 3, 1999. No published date.

Akasaka, Takeshi, et al. Singlet Oxygen Oxidation of Organophosphorus Compounds: Cooxidation of Olefin with Phosphadioxirane. Quimica Nova, 1993, 16, pp. 325-327. No published date or location.

Milner, O.I., et al. Determination of Trace Materials in Crudes and Other Petroleum Oils. Analytical Chemistry, vol. 24, No. 11. Published Nov. 1952, USA.

Aida, Tetsuo, et al. Development of an Efficient Coal-Desulfurization process: "Oxy-Alkalinolysis". Technical Report Resource Conference: American Chemical Society symposium on coal liquefaction, pp. 328-334. Kansas City, MO USA. Published Sep. 1, 1982 Ames Lab., IA (USA); Advanced Fuel Research, Inc., East Hartford, CT (USA).

Aida, Tetsuo, et al. Reaction of Dibenzothiophene Sulfone with Alkoxides. Tetrahedron Letters (1983), vol. 24, No. 34, pp. 3543-3546. USA.

Oviedo, Alberto, et al. Deoxydesulfurization of sulfones derived from dibenzothiophene using nickel compounds. Journal of Molecular Catalysis A: Chemical, (2008) 293, pp. 65-71. USA.

U.S. Appl. No. 12/904,446, filed Oct. 14, 2010.

Application No. PCT/US08/82095, International Search Report and the Written Opinion of the International Searching Authority, or the Declaration dated Mar. 20, 2009. 12 pages.

Application No. PCT/US11/50159, International Search Report and the Written Opinion of the International Searching Authority dated Jan. 12, 2012. 11 pages.

Notice of Allowance (Mail Date Feb. 13, 2012) for U.S. Appl. No. 12/904,446, filed Oct. 14, 2010.

Notice of Allowance (Mail Date Mar. 22, 2012) for U.S. Appl. No. 12/888,049, filed Sep. 22, 2010.

* cited by examiner

Figure 2

| Specie Name | Molecular Structure | Bp (°F/°C) | Molecular Weight |
|---|---|---|---|
| Mercaptans | RSH | N/A | N/A |
| Sulfides | RSR' | N/A | N/A |
| Disulfides | RSSR' | N/A | N/A |
| Thiophenes | (structure) | 180/84 | 84 |
| Benzothiophenes | (structure) | 430/221 | 134 |
| Dibenzothiophenes | (structure) | 630/332 | 184 |
| Benzo-Naphthothiophenes | (structure) | 700/371 | 234 |

Generalized Structure of Polymeric Catalyst

On Surface & Inside Pores

Integrated w/in Support

Figure 10. A graphic depiction for the reaction mechanism of olefins with peracids

Figure 12. Pseudo-1st Order Plot for the Oxidation of Benzothiophenes (26:1 Oxidant:S ratio, 9700 S:Ti ratio, 2 Acetic Acid: Oil mass ratio)

SULFOXIDATION CATALYSTS AND METHODS AND SYSTEMS OF USING SAME

CROSS-REFERENCE TO RELATED APPLICATIONS

This application is a continuation-in-part of and claims priority from co-pending U.S. Provisional Application No. 61/039,619 filed Mar. 26, 2008 and entitled SULFOXIDATION CATALYSTS AND METHODS, the disclosure of which is hereby incorporated by reference to the extent not inconsistent the present disclosure.

FIELD OF THE DISCLOSURE

The disclosure generally relates to catalyst compounds, catalytic processes, and methods for synthesizing catalytic compounds. Specifically, the disclosure relates to sulfoxidation reactions, catalysts for sulfoxidation, methods of synthesis of sulfoxidation catalysts, and systems and methods of catalytic sulfoxidation reactions.

BACKGROUND OF THE DISCLOSURE

A globally recognized need to reduce sulfur levels in hydrocarbon streams such as gasoline and diesel fuels currently exists. The reduction of sulfur in such hydrocarbon streams may greatly improve air quality because of the negative impact sulfur has on performance of sulfur sensitive components such as automotive catalytic converters. The presence of oxides of sulfur in automotive engine exhaust may inhibit and eventually poison noble metal catalysts within catalytic converters and emission of those oxides of sulfur can have a negative impact on the environment. Emissions from inefficient or poisoned catalytic converters contain levels of many other undesirable materials, such as: non-combusted-non-methane hydrocarbons, oxides of nitrogen, and carbon monoxide. Such emissions may be photoconverted by sunlight generating ground level ozone, known also as smog.

Thermally processed gasolines such as, for example, thermally cracked gasoline, visbreaker gasoline, coker gasoline and catalytically cracked gasoline (hereinafter collectively referred to as "cracked gasoline") contain, in part, olefins, aromatics, sulfur, and sulfur-containing compounds. Given that most gasolines, such as, automobile gasolines, racing gasolines, aviation gasolines, boat gasolines, and the like contain blends of, at least in part, cracked gasoline, reduction of sulfur in cracked gasoline will inherently facilitate reduction of sulfur levels in most gasolines, including: automobile gasolines, racing gasolines, aviation gasolines, boat gasolines, and the like.

There is a growing public recognition that lower sulfur gasoline reduces automotive emissions and improves air quality. Thus, the US Environmental Protection Agency rules to date have focused on the required level of reduction, the geographical areas in need of lower sulfur gasoline, and the time frame for implementation.

As the concern over the impact of automotive air pollution continues, it is clear that further effort to reduce the sulfur level in automotive fuels will be required. In 2008, the US Environmental Protection Agency standards will effectively require every blend of gasoline sold in the United States to meet a 30-ppm sulfur level.

In addition to the need to be able to produce low sulfur content automotive fuels, there is also a need for the implementation of systems and processes that will have a minimal effect on the olefin content of such fuels so as to maintain the octane number (both research and motor octane number). Such systems and processes would be desirable since saturation of olefins greatly affects the octane number. Such adverse effect on the olefin content is generally due to the severe conditions normally employed, such as during hydrodesulfurization, to remove thiophenic compounds (such as, for example, thiophenes, benzothiophenes, alkyl thiophenes, alkylbenzothiophenes, alkyl dibenzothiophenes and the like) which are some of the most difficult sulfur containing compounds to remove from cracked gasoline. In addition, there is a need to avoid systems and processes wherein the conditions are such that the aromatic content of the cracked gasoline is lost through saturation. Thus, there is a need for systems and processes that achieves desulfurization and maintains the octane number.

However, current processes may have adverse effects on the olefin content which may be generally due to the severe conditions normally employed, such as during hydrodesulfurization, to remove thiophenic compounds (such as, for example, thiophenes, benzothiophenes, alkyl thiophenes, alkylbenzothiophenes, alkyl dibenzothiophenes and the like). In removing sulfur from diesel fuels by hydrodesulfurization, the cetane number is typically improved; however there is a large cost in hydrogen consumption, since hydrogen is consumed by both hydrodesulfurization and aromatic hydrogenation reactions.

In addition to the need for removal of sulfur from cracked gasolines, there is also a need for the petroleum industry to reduce the sulfur content in diesel fuels. In general, it is much harder to remove sulfur from diesel fuel as compared to gasoline. Further, the high-pressure and high temperature required by hydro desulfurization requires expensive capital equipment infrastructure and high operating cost to achieve mandated low levels of sulfur.

Thus, there is a need for a desulfurization system and process without a significant consumption of hydrogen so as to provide a more economical process for the treatment of cracked gasolines and diesel fuels.

Some prior art catalysts include harsh acids, such as sulfuric acid, which are difficult to separate from the reaction mixture and have demonstrated incomplete conversion of desired reaction components. Transition metal catalysts are typically more facile to separate from the reaction mixture owing to their substantially different physical and chemical properties. Solid state heterogeneous catalysts are particularly facile to separate from liquid and gaseous reaction mixtures.

As a result of the lack of success in providing a successful and economically feasible process for the reduction of sulfur levels in cracked gasolines and diesel fuels combined with the fact that crude oil supplies are growing more sour (sulfur-rich) each day, it is apparent that there is a need for better catalyst systems and processes for the desulfurization of such hydrocarbon streams which have minimal effect on octane levels while achieving high levels of sulfur removal.

Thus, there exists a need for an economical and efficient catalytic desulfurization process for the treatment of sulfur-containing hydrocarbon streams, e.g., crude and crude oil distillates.

SUMMARY OF THE DISCLOSURE

A first aspect of the disclosure relates to a sulfoxidation method comprising: providing a hydrocarbon stream including at least one sulfur compound; providing an oxidant; providing a catalyst comprising a metal compound represented by the general formula $M_mO_m(OR)_n$; and contacting the hydrocarbon stream with the oxidant in the presence of the catalyst, resulting in the oxidation of the at least one sulfur compound.

A second aspect of the disclosure relates to a polymeric catalyst composition prepared by the reaction of Q-R-Q' with a bis(polyol)oxotitanium(IV) catalyst, wherein Q and Q' each independently comprise an isocyanate, anhydride, sulfonyl halide, benzyl halide, carboxylic acid halide, phosphoryl acid halide, silyl chloride, or any chemical functionality capable of reacting with the —OH pendant group of the catalyst, and wherein R comprises a linking group.

A third aspect of the disclosure relates to a catalytic sulfoxidation reagent comprising: a phase transfer agent/solvent; a catalyst comprising a metal complex represented by the general formula $M_mO_m(OR)_n$ dissolved in the phase transfer agent/solvent; and an oxidant dissolved in the phase transfer agent/solvent A fourth aspect of the disclosure relates to a sulfoxidation process comprising the acts of: providing at least a first combination mixing point/reactor/injection point; providing a sulfur-rich hydrocarbon fluid stream; delivering the sulfur-rich hydrocarbon fluid stream to at least a first combination mixing point/reactor/injection point; providing an oxidant; delivering the oxidant to the at least a first combination mixing point/reactor/injection point; mixing the oxidant with the hydrocarbon fluid stream at the at least a first combination mixing point/reactor/injection point to produce a mixture; providing a polar protic fluid stream; providing a catalyst; combining the mixture with the polar protic fluid stream in the presence of the catalyst to form a reaction mixture, the combining act resulting in the sulfoxidation of sulfur-rich organic fluid within the at least first mixing point/reactor/injection point; providing at least a first combination separator/dryer; transferring the mixture stream from the at least a first combination mixing point/reactor/injection point to the at least a first combination separator/dryer; separating at least a first substantially sulfur-free hydrocarbon product stream from a sulfur-rich hydrocarbon stream and the wet polar protic fluid stream; drying the wet polar protic fluid stream in the first combination separator/dryer; returning the dried polar protic fluid stream to the at least first mixing point/reactor/injection point; providing at least a second reactor; transferring the sulfur-rich hydrocarbon stream to the second reactor; heating the sulfur rich hydrocarbon stream in the second reactor, the heating resulting in at least a second substantially sulfur-free organic stream and a sulfur-enriched coke stream; providing at least a first combination mixing point/separator; combining the two substantially sulfur-free streams at the at least a first combination mixing point/separator; and separating the resulting combination into a substantially sulfur-free, olefin rich hydrocarbon product stream.

BRIEF DESCRIPTION OF DRAWINGS

The features of the disclosure are set forth in the appended claims. The disclosure itself, however, will be best understood by reference to the following detailed description of illustrative embodiments when read in conjunction with the accompanying drawings, wherein:

FIG. 2 is a chart illustrating typical molecular structures of organosulfur compounds found in petroleum products.

FIGS. 6A1-3 are a general graphic depiction of the catalyst of the present disclosure on a surface of a modified polystyrene bead, with three different commercially available reactive linker functionalities, that interact in a fashion to bind the titanium catalyst to the surface according to the present disclosure.

FIG. 6B is a generalized graphic depiction of the structure of the surface bound titanium catalyst, as described in 6A1-3 in a general form, where the linker may be any linker that undergoes a chemical reaction with the hydroxy moiety of the catalyst, such that it produces a polystyrene connected chemical moiety.

FIG. 6C is an even more general graphic depiction of a surface bound catalyst of the present disclosure, where the surface may be any other surface that has a chemical reactive linker that can also react with the hydroxy moiety in a similar fashion as those described in 6A1-3.

FIG. 6D is an even more generalized graphic description of the present disclosure of a surface bound catalyst, wherein the hydroxy moiety of the catalyst of the present disclosure may be connected in any chemical fashion to a surface.

DETAILED DESCRIPTION OF THE DISCLOSURE

Figure 1:
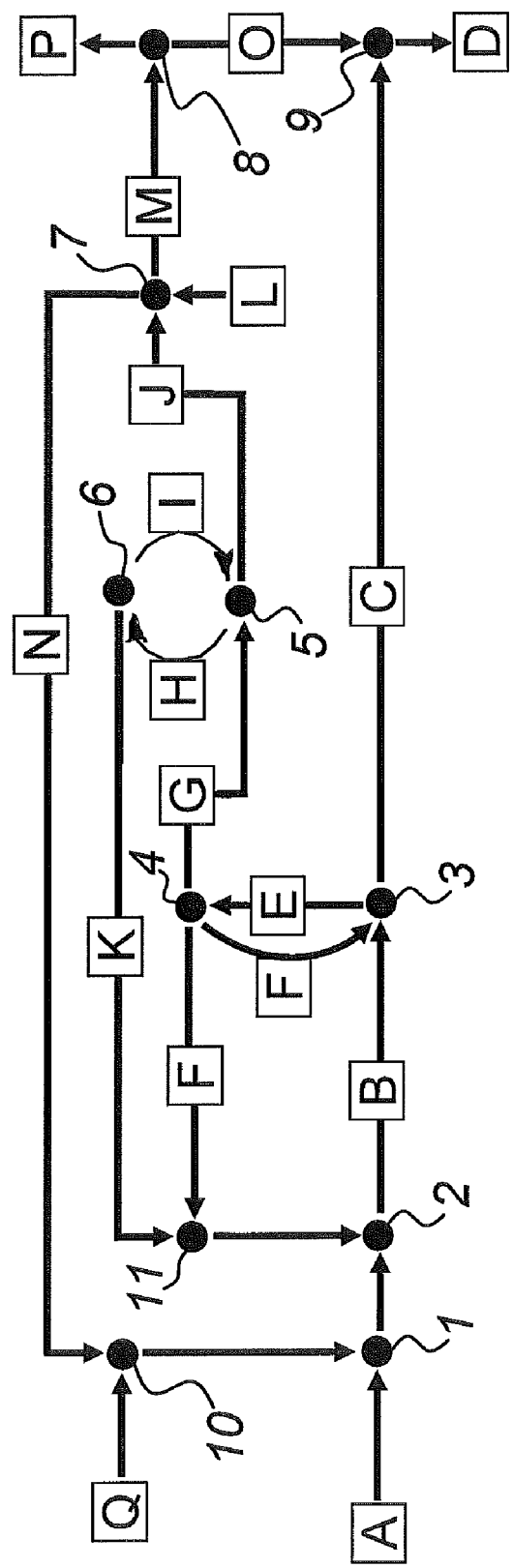
FIG. 1 is a process flow diagram of an embodiment of a sulfoxidation process, in accordance with embodiments of the present disclosure.

While this disclosure contains many specific details, it should be understood that various changes and modifications may be made without departing from the scope of the technology herein described. The scope of the technology shall in no way be construed as being limited to the number of constituting components, the concentration of constituting components, the materials thereof, the shapes thereof, the relative arrangement thereof, the temperature employed, the order of combination of constituents thereof, etc., and are disclosed simply as examples. The depictions and schemes shown herein are intended for illustrative purposes and shall in no way be construed as being limiting in the number of constituting components, connectivity, reaction steps, the materials thereof, the shapes thereof, the relative arrangement thereof, the order of reaction steps thereof, etc., and are disclosed simply as an aid for understanding. The examples described herein relate to the removal of sulfur from hydrocarbon streams and they relate to catalysts suitable for use in the oxidative desulfurization of fluid streams of crude oil, diesel fuels, and cracked gasolines (e.g. thermally processed gasoline such as thermally cracked gasoline, visbreaker gasoline, coker gasoline and catalytically cracked gasoline). In addition, the examples described herein relate to methods for the removal of sulfur compounds from fluid streams of cracked gasoline and diesel fuels employing metal catalysts.

In general, "substituted" as used herein refers to an alkyl, cycloalkyl, cycloalkylalkyl, heterocyclyl, or heterocyclylalkyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, heterocyclyloxy, and heterocyclylalkoxy groups; carbonyls (oxo); carboxyls; esters; ethers; urethanes; alkoxyamines; thiols; sulfides; sulfoxides; sulfones; sulfonyls; sulfonamides; amines; N-oxides; isocyanates; cyanates; thiocyanates; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with substituted or unsubstituted alkyl or alkenyl groups as defined below.

Alkyl groups include straight chain and branched alkyl groups having from 1 to about 20 carbon atoms or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups can be substituted at the alkyl, the cycloalkyl or both the alkyl and cycloalkyl portions of the group. Representative substituted cycloalkylalkyl groups can be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6 to 14 carbons, and in others from 6 to 12 or even 6 to 10 carbon atoms in the ring portions of the groups Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups can be substituted at the alkyl, the aryl or both the alkyl and aryl portions of the group. Representative aralkyl groups include but are not limited to benzyl and phenethyl groups and fused (cycloalkylaryl) alkyl groups such as 4-ethyl-indanyl. Representative substituted aralkyl groups can be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. However, the phrase "heterocyclyl group" does not include heterocyclyl groups that have other groups, such as alkyl, oxo or halo groups, bonded to one of the ring members.

Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above and further including, but not limited to, fused ring substitutions, for example, dibenzothiophenes and benzo-naphthothiophenes are fused ring variants of the benzothiophenyl group listed above, and their even further representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups can be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups can be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups can be substituted one or more times with substituents such as those listed above.

Embodiments described herein relate to the removal of sulfur from hydrocarbon streams. Embodiments described herein relate to catalysts suitable for use in the oxidative desulfurization of hydrocarbon fluid streams of crude oil, diesel fuels, and cracked gasolines (e.g. thermally processed gasoline such as thermally cracked gasoline, visbreaker gasoline, coker gasoline and catalytically cracked gasoline) and distillates derived therefrom. Embodiments described herein relate to systems and methods for the removal of sulfur compounds from fluid streams of cracked gasoline and diesel fuels employing the above catalysts. Embodiments described herein also relate to fuel products and lubricants derived from the catalyst treated hydrocarbon fluid streams described in the present disclosure.

The catalyst compositions described herein may comprise metal complexes. In some embodiments, the metal complex may be represented by the formula $M_mO_m(OR)_n$, where M is a metal complex, such as, for example, titanium or any metal, including, but not limited to, rhenium, tungsten or other transition metals alone or in combination that causes the chemical conversion of the sulfur species, as described herein. R is carbon group having at least 3 carbon atoms, where at each occurrence R may individually be a substituted alkyl group containing at least one OH group, a substituted cycloalkyl group containing at least one OH group, a substituted cycloalkylalkyl group containing at least one OH group, a substituted heterocyclyl group containing at least one OH group, or a heterocyclylalkyl containing at least one OH group. The subscripts m and n may each independently be integers between about 1 and about 8. R may be substituted with halogens such as F, Cl, Br, and I. In some embodiments, the metal alkoxide comprises bis(glycerol)oxotitanium(IV)), where M is Ti, m is 1, n is 2, and R is a glycerol group. Other examples of metal alkoxides include bis(ethyleneglycol)oxotitanium (IV), bis(erythritol)oxotitanium (IV), and bis(sorbitol)oxotitanium (IV). The catalysts described herein may be used singly or in combinations in the catalyzed reactions described herein where metal M is any metal that causes the chemical conversion of the sulfur species, as described herein.

There is a right here in may further comprise a metal complex containing polymer. In some embodiments, the metal complex containing Polymer may be represented graphically by FIGS. 6-9.

In some embodiments, the catalysts described herein may be contacted with an organic fluid (such as a hydrocarbon) solution or stream containing at least one sulfur compound, in the presence of an oxidant (oxidizing agent), resulting in the catalyst catalyzing the oxidation of the sulfur compound, resulting in the oxidized sulfur compound having a higher solubility in the catalyst solution than in hydrocarbon fluid. Examples of suitable organic fluids include, but not limited to, gasolines (including cracked gasolines described above), diesel fuel, jet oils, heavy oils, heavy sour crude oil, other derived products typical of petroleum refinery products and intermediates, and combinations thereof. Examples of sulfur compounds include, but are not limited to, alkyl-thios, aromatic-thiols, aromatic-sulfides, aromatic-sulfoxides, alkyl-thiophene, aromatic-thiophenes, other refractory sulfur-containing compounds, and combinations thereof.

The catalysts described herein may be utilized in biphasic reaction processes, wherein the sulfur compounds are at least partially extracted out of the organic fluid and into the aqueous phase, resulting in leaving the hydrocarbon fluid essentially sulfur free or at a reduced sulfur concentration. Examples of suitable phase transfer agent/solvents include polar protic liquids such as acetic acid, formic acid, propanoic acid, octenoic acid, butenoic acid, long chain aliphatic acids, alkyl substituted aromatic acids, the like, and combinations thereof. Examples of suitable oxidants include, but are not limited to, $O_3$, $H_2O_2$, NaOCl, $O_2$, air, permanganate compounds, nitrous oxide, other suitable oxidants that readily react with the catalyst to cause the sulfoxidation reaction to occur according to the present disclosure. The oxidant may be delivered in the form of a solid, a liquid or a gas, and combinations thereof.

The reaction described herein may be carried out within a temperature range from about 20° C. to about 90° C., such as between about 20° C. and about 50° C. Higher reaction temperatures may accelerate the rate of reaction between the sulfur compound and the oxidant. Reaction schemes using temperatures higher than 90° C. may be hindered by non-productive decomposition of some oxidants, such as peroxides.

The concentration of catalyst may be in a range from about 100.00% to 0.00004% by weight with respect to elemental sulfur, such as from about 100.00% to about 0.0004% by weight with respect to the weight of elemental sulfur. The catalyst may be present in homogeneous form (such as dissolved in an alcohol then added to the polar protic phase, for example) or heterogeneous form (such as a solid, such as in cases where the catalyst has a low solubility in the phase transfer agent/solvent). The solid catalysts as described herein may comprise any suitable form which affords efficient catalytic activity. For example, a catalyst may comprise a complex, a cluster complex, a mixture of isomers, a nano-dimensional material, a metal complex containing polymer or a combination thereof. Nano-dimensional materials may comprise nanoparticles of the catalyst, where the nanoparticles may be produced by controlled hydrolysis. The nanoparticles may be sintered following formation. Nanoparticles thus produced may be used as components of organic solutions, suspensions, and composites, and the like.

In some embodiments, a hydrocarbon fluid containing a sulfur compound may be brought into contact with a transfer agent/solvent containing the catalyst, in the presence of an oxidant. The catalyst may catalyze the oxidation of the sulfur compound, resulting in converting it to a compound which is soluble in the transfer agent/solvent, where the oxidized sulfur compound may then be extracted and removed from the hydrocarbon fluid. The fluid may be contacted with the catalyst solution in a continuous process or in a batch process. For example, a hydrocarbon stream (containing the sulfur compound) may be contacted with the catalyst solution at a location within a fixed bed reactor or at a location a flowing bed reactor for sufficient residence time to allow conversion (oxidation) of the sulfur compound to occur, followed by separation of the essentially sulfur-free hydrocarbon stream from the now sulfur-containing catalyst stream. The two separate phases may then be separated and materials (such as catalyst and solvents) may be recycled as needed.

FIG. 1 is a process flow diagram of an embodiment of a sulfoxidation process such as those described above. Source A may comprise a sulfur-rich organic fluid stream input into the process at mixing point 1, where the organic fluid may be a fluid such as those described above. Source Q may comprise an oxidant introduced into the system at injection point 10, where the oxidant may comprise oxidants described above, where the oxidant mixes with the organic fluid stream at mixing point 1. Source Q may comprise an electric input in embodiments where the oxidant is produced by electrolysis.

The mixture from mixing point 1 may be combined with a catalyst in reactor 2 to form a biphasic oil-reaction mixture, resulting in the sulfoxidation of the sulfur-rich organic fluid within reactor 2. The catalyst may be those described above. The catalyst may enter the reactor 2 as a solid or liquid, and may be transferred to reactor 2 from mixing point 11. In some embodiments, the mixing performed at mixing points 1 and 11 may be performed at reactor 2, and reactor 2 may be a static mixer or a fixed bed reactor, continuously stirred reactor, when the catalyst is a solid, and the reagent mixtures are liquids and other known methods of performing catalytic biphasic reactions.

A biphasic oil-reaction stream B may be transferred from reactor 2 to separator 3, where a sulfur-rich polar extractate E may be separated from low-sulfur (or essentially sulfur-free) raffinate C. The sulfur-rich extractate E (comprising oxidized sulfur compounds and catalyst solution) may be transferred from the separator 3 to a distillation tower 4, where distillate overheads F (substantially pure extractant, such as solvent) may be separated via distillation from distillate heavies G, where distillate heavies may comprise oxidized sulfur compounds (such as organic sulfones) and catalyst. In some embodiments, separator 3 and distillation tower 4 can be combined into a single distillation tower. Distillate overheads F may be returned to mixing point 11 or to separator 3. Distillate overheads F recirculated to separator 3 may further extract sulfur compounds in separator 3, resulting in raffinate C being essentially sulfur-free. In some embodiments, the sulfur-rich extractate E may represent about 15% by weight of the biphasic oil-reaction stream B and the low-sulfur (or essentially sulfur-free) raffinate C may represent about 85% by weight of the biphasic oil-reaction stream B.

Distillate heavies G may be transferred to extractor 5, where catalyst may be extracted through process H using distillation tower 6, and solvent may be returned to extractor 5 through process I. Catalyst concentrate K may be returned to mixing point 11. The remaining sulfur-rich, salt-containing heavies J may be transferred from extractor 5 to extractor 7, where salts may be removed through aqueous wash output N and returned to reactor 10. Where the oxidant is NaOCl, the process at extractor 7 may comprise a salt extraction. Extractor 7 may comprise a solvent wash when other oxidants are used. Water may be introduced into extractor 7 through input L.

The sulfur rich heavy stream M (e.g., sulfur-rich organics) may be transferred from extractor 7 to reactor 8. Reactor 8 may comprise a high temperature reactor and may utilize a catalyst, such as a solid bed catalyst. At reactor 8, the sulfur rich heavies may be catalytically fractioned into $SO_2$ and organic compounds, where $SO_2$ may be removed from reactor 8 at $SO_2$ output P as a gas. Recovered organic compounds O produced in reactor 8 (e.g. oil, etc.) may be transferred from reactor 8 to mixing point 9 where the organic compounds O are mixed with the substantially low-sulfur raffinate C and may be transferred to low sulfur hydrocarbon product stream output D

EXAMPLES

One Possible Embodiment of the Preparation of Bis (Glycerol) Oxotitanium (IV)

Titanium oxychloride (2 kilograms (kg), Millenium Chemicals) was diluted with de-ionized water (2 kg) and then added to a 20 liter (l) round bottom flask containing glycerine (2 kg). The mixture was allowed to stir until a straw color was attained. The 20 l round bottom flask was then heated to 50° C. under vacuum (−25 inches Hg) in a rotary evaporator to remove excess water and hydrochloric acid. When no further liquid condensate was noted, the flask was recharged with water (0.65 l) and rotary evaporated to further remove excess water and hydrochloric acid. This was repeated two additional times. After the final evaporation, the viscous, straw colored liquid was weighed (2.64 kg) and diluted with methoxypropanol (0.85 kg) to reduce the viscosity. This was then neutralized with triethylamine (3.3 kg, 33% weight/weight in ethanol). The combined neutralized solution was then chilled for several hours producing rod-like needles of triethylamine hydrochloride. The crystalline triethylamine hydrochloride was removed by vacuum filtration. The filtrate was added slowly to acetone (70 L) causing the product to precipitate as a white solid. The acetone was then decanted and an off-white solid residue was obtained. The off-white solid residue was then washed vigorously with hexanes (20 L) to afford a fine white powder. The powder was collected by filtration (>63% yield based upon Ti). % Ti Calculated: 16.98. Analysis: 16.7; mp DSC (dec) 273° C.; ESI-MS (positive mode) 245 amu; $^1$H-NMR (DMSO-d6) 4.25 (br s, 4H), 3.45 (m, 2H), 3.38 (m, 4H), 3.31 (m, 4H).

One Possible Embodiment of the Preparation of Polymeric Titanyl Complexes

Dimethyl sulfoxide (DMSO) was added to a 120-250 mL glass bottle containing a stir bar. The monomer was added to the DMSO, followed by bis(glycerol)oxotitanium(IV), added in a 1:1 mole ratio relative to the monomer. The slurry was heated with stirring in a water bath set at 70° C. for 1-4 hrs, after which time the mixture turned into a transparent solution. After cooling to room temperature, the mixture was transferred to a beaker and the product was precipitated using 5x acetone. After approximately 10-20 minutes, the precipitate was collected by vacuum filtration and dried overnight in a vacuum oven. Yields are about 90+%.

General Method A

Model oil was prepared by dissolving dibenzothiophene (DBT) in tetralin to give solutions with sulfur contents of about 15000 parts per million (ppm) (approximately 0.76 grams of DBT dissolved in 8.33 grams of tetralin). The oxidative desulfurization experiments were carried out by combining acetic acid with the model oil in a glass batch reactor, adding a measured aliquot of a 40% by weight solution of titanyl sulfoxidation catalyst, bis(glycerol)oxotitanium(IV), in methanol and then adding a measured quantity of the oxidant. A heated circulating bath was used to control temperature (±0.1K) of the reactor (J-KEM), typically set at 323 K (50° C.). Aliquots of the oil phase were withdrawn at various time intervals and measured by chromatographic techniques for extent of conversion of the DBT. The reactions were stirred with a mixing bar speed of about 200 revolutions per minute (rpm).

General Method B

Model oil was prepared by dissolving dibenzothiophene (DBT) in tetralin to give solutions with sulfur contents of approximately 15000 ppm (approximately 0.76 grams of DBT dissolved in 8.33 grams of tetralin). The oxidative desulfurization experiments were carried out by combining acetic acid and the solid catalyst with the model oil in a glass batch reactor, and then adding a measured quantity of the oxidant. A heated circulating bath was used to control temperature (±0.1K) of the reactor (J-KEM) typically set at 323 K (50° C.). Aliquots of the oil phase were withdrawn at various time intervals and measured by chromatographic techniques for extent of conversion. The reactions were stirred with a mixing bar speed of about 200 revolutions per minute (rpm).

General Method C

Model oil was prepared by dissolving dibenzothiophene (DBT) in tetralin to give solutions with sulfur contents of 15000 ppm. The oxidative desulfurization experiments were carried out by combining acetic acid and a measured aliquot of a 40% by weight solution of catalyst in methanol and then adding a measured quantity of the oxidant to the model oil in a glass-lined pressure reactor. The reaction was heated in a circulating bath to control temperature (±0.1K, J-KEM) typically set at 323 K (50° C.). Reaction time started upon pressurization with air. The reaction was stopped at various time intervals and analyzed by chromatographic techniques for extent of conversion. The reactions were stirred with a mixing bar speed of about 200 revolutions per minute (rpm).

General Method D

Oxidative desulfurization of raw diesel (21100 ppm sulfur) was carried out by combining glacial acetic acid and aliquots of titanium catalyst solution (40 wt % in methanol) and hydrogen peroxide with the diesel in a glass batch reactor. A heated circulating bath was used to control the temperature (323 K, ±0.1K) of the reactor (J-KEM). The reactions were stirred with a mixing bar speed of about 400 revolutions per minute (rpm) for 30-60 minutes. The diesel phase was removed from the acid phase using a 1000-mL separatory funnel. The diesel was then extracted three times with fresh glacial acetic acid. Residual acetic acid in the diesel was removed by rotary evaporation. The sulfur content of the diesel was monitored over each step of the ODS process using an XOS Sindie 7039 XR X-ray fluorescence spectrometer.

General Method E

A model oil was prepared by dissolving benzothiophene (BT), dibenzothiophene (DBT), 4-methyldibenzothiophene (MDBT), and 4,6-dimethyldibenzothiophene (DMDBT) in tetralin (~500 ppm S). The oxidative desulfurization experiments were carried out by combining acetic acid with the model oil in a glass batch reactor, adding 40% catalyst in MeOH solution and then adding a measured quantity of the oxidant ($H_2O_2$). A heated circulating bath was used to control temperature of the reactor. Aliquots of the oil phase were withdrawn at various time intervals and measured by chromatographic techniques for extent of conversion of the four sulfur components. The reactions were stirred with a mixing bar speed of about 400-450 revolutions per minute (rpm).

General Method F

A model oil was prepared by dissolving dibenzothiophene (DBT) in tetralin (1-2% S). The oxidative desulfurization experiments were carried out by combining acetic acid (5× oil phase) with the model oil in a glass batch reactor, adding varying amounts of catalyst and then adding a measured quantity of the oxidant ($H_2O_2$) (2-5.5 molar equivalents). A heated circulating bath was used to control temperature of the reactor. Aliquots of the oil phase were withdrawn at various time intervals of some experiments and measured by chromatographic techniques for extent of conversion of the sulfur component. The reactions were stirred with a mixing bar speed of about 400-450 revolutions per minute (rpm).

General Method G

Figure 12:
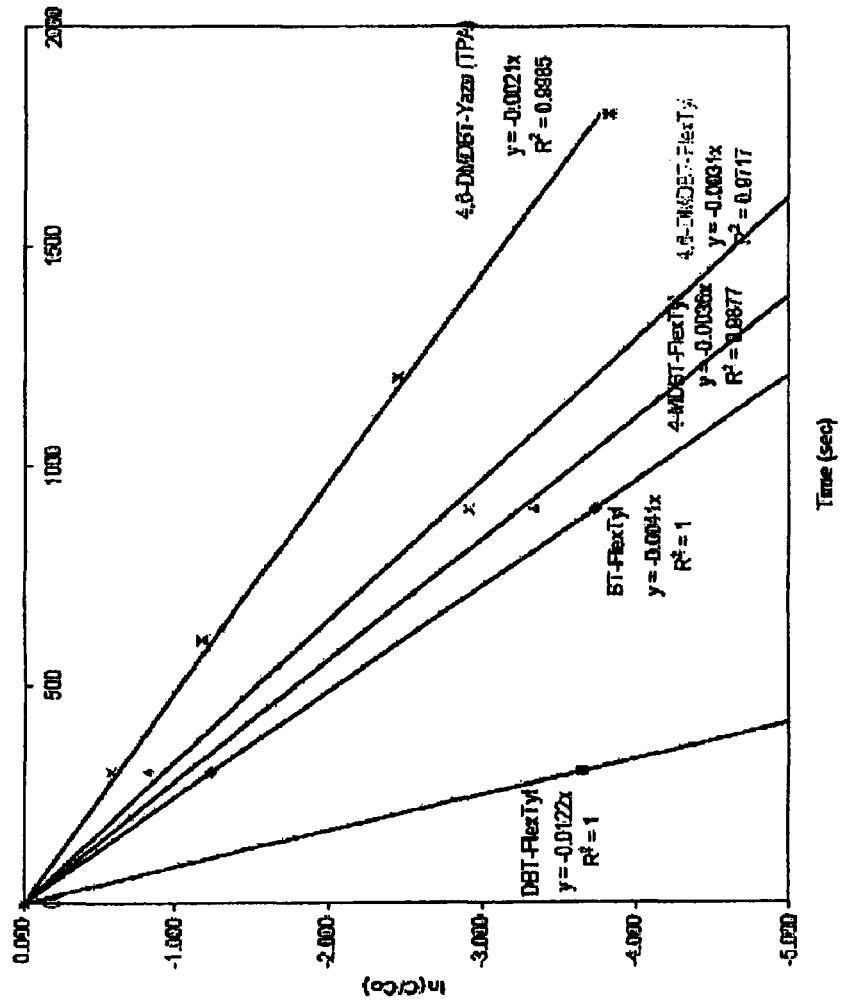
FIG. 12 is a graphic illustration of chemical kinetics experiments performed in accordance with the present disclosure.

Model oil was prepared by dissolving DBT (72.4 mg, 0.39 mmoles), benzothiophene (BT) (54.1 mg, 0.4 mmoles), 4-methyldibenzothiophene (4-MDBT) (81.0 mg, 0.41 mmoles), and 4,6-dimethyldibenzothiophene (DMDBT) (78.5 mg, 0.37 mmoles) in decalin. The oxidation experiment was carried out by combining acetic acid (12 g) with the model oil in a glass batch reactor, adding 100 µl of a 40% by weight solution of bis(glycerol)oxotitanium(IV) in methanol and then adding 2.8 grams of 50% $H_2O_2$ solution (26:1 O:S ratio). A heated circulating bath was used to control temperature (±0.1K) of the reactor (J-KEM), typically set at 323 K (50° C.). The experiment was run for a half hour with aliquots pulled at 5, 15, and 30 minute intervals (full phase separation was allowed to occur at which point sampling was taken and time noted). The data is shown in FIG. 12 plotted in comparison to the results of Tungstophosphoric acid (TPA) (Yazu).

Examples 1-18

Reactions were run varying catalyst volume (Vol.), oxidant level (Oxidant, $H_2O_2$ concentration), acid strength (Acid, 25% acetic vs Glacial Acetic), and temperature (T) according to General Method A and analyzed for percent conversion (% yield) after 1 hour. The catalyst was a methanol solution of bis(glycerol)oxotitanium(IV). The volume of acid was between about 8.35 and about 8.37 g. The amount of oxidant was about 2.80 g. The results obtained are shown below in Table 1.

TABLE 1

| run | Acid | Vol. | Oxidant | T | % yield |
|---|---|---|---|---|---|
| 2 | 25% acetic | 10 µl | $H_2O_2$ (25%) | 50° C. | 16.6 |
| 4 | Glacial acetic acid | 10 µl | $H_2O_2$ (25%) | 50° C. | 40.9 |
| 6 | 25% acetic | 100 µl | $H_2O_2$ (25%) | 50° C. | 1.9 |
| 8 | Glacial acetic acid | 100 µl | $H_2O_2$ (25%) | 50° C. | 100 |
| 10 | 25% acetic | 10 µl | $H_2O_2$ (50%) | 50° C. | 1.4 |
| 12 | Glacial acetic acid | 10 µl | $H_2O_2$ (50%) | 50° C. | 96.4 |
| 14 | 25% acetic | 100 µl | $H_2O_2$ (50%) | 50° C. | 3.6 |
| 16 | Glacial acetic acid | 100 µl | $H_2O_2$ (50%) | 50° C. | 100 |
| 17 | Glacial acetic acid | 100 µl | $H_2O_2$ (50%) | 50° C. | 100 |
| 18 | Glacial acetic acid | 100 µl | $H_2O_2$ (50%) | 50° C. | 100 |
| 1 | 25% acetic | 10 µl | $H_2O_2$ (25%) | RT | 0 |
| 3 | Glacial acetic acid | 10 µl | $H_2O_2$ (25%) | RT | 3.9 |
| 5 | 25% acetic | 100 µl | $H_2O_2$ (25%) | RT | 0.2 |
| 7 | Glacial acetic acid | 100 µl | $H_2O_2$ (25%) | RT | 28.3 |
| 9 | 25% acetic | 10 µl | $H_2O_2$ (50%) | RT | 0 |
| 11 | Glacial acetic acid | 10 µl | $H_2O_2$ (50%) | RT | 9 |
| 13 | 25% acetic | 100 µl | $H_2O_2$ (50%) | RT | 0.3 |
| 15 | Glacial acetic acid | 100 µl | $H_2O_2$ (50%) | RT | 89.8 |

Example 19

Example 16 (above) was repeated drawing aliquots for analysis at 10 minute intervals for 40 minutes. The results obtained are shown below in Table 2:

TABLE 2

| Time (minutes) | % Conversion |
|---|---|
| 10 | 63.4 |
| 20 | 98.8 |
| 30 | 100 |
| 40 | 100 |

Example 20

Example 19 (above) was repeated except that the spin rate was doubled from about 200 rpm to about 400 rpm. For the reactions described herein, the mixing speed of the reactions may be optimized to produce maximum intermixing of reactant. Aliquots were withdrawn for analysis at 5, 15, and 25 minutes to measure the effect. The results obtained are shown below in Table 3.

TABLE 3

| Time (min) | % Conversion |
|---|---|
| 5 | 50.6 |
| 15 | 99.2 |
| 25 | 100 |

Example 21

Example 20 (above) was repeated except that the mass ratio of acetic acid to tetralin was doubled. Aliquots were withdrawn for analysis at 5, 10, and 12 minutes to measure the effect. The results obtained are shown below in Table 4.

TABLE 4

| Time (min) | % Conversion |
|---|---|
| 5 | 99.3 |
| 10 | 100 |
| 12 | 100 |

Example 22

Example 20 (above) was repeated except that the concentration of hydrogen peroxide was reduced to 3 mole equivalents with respect to DBT. Aliquots were withdrawn for analysis at 5, 15, and 25 minutes to measure the effect. The results obtained are shown below in Table 5.

TABLE 5

| Time (min) | % Conversion |
|---|---|
| 5 | 84.4 |
| 15 | 100 |
| 25 | 100 |

Example 23

Example 20 (above) was repeated except air was used as the oxidant at ambient pressure according to General Method C. After 87 hours, the reaction achieved 0.6% conversion.

Example 24

Example 23 (above) was repeated except air was used as the oxidant at 150 psi according to General Method C. After 1 hour, the reaction achieved 0.6% conversion.

Examples 25-41

Reactions were run varying amount of catalyst volume (wt.), oxidant level (Oxidant, $H_2O_2$ concentration), acid strength (Acid, 25% acetic vs Glacial Acetic), and temperature (T) according to General Method B and analyzed for percent conversion (% yield) after 1 hour. The temperature RT represents room temperature, approximately 20° C. The catalyst was solid bis(glycerol)oxotitanium(IV). The volume of acid was between about 8.34 and about 8.38 g. The amount of oxidant was about 2.80 g. The results obtained are shown below in Table 6.

TABLE 6

| run | Acid | wt | Ox | T | % yield |
|---|---|---|---|---|---|
| 25 | 25% acetic | 8.6 mg | $H_2O_2$ (25%) | 50° C. | 0 |
| 26 | Glacial acetic acid | 8.5 mg | $H_2O_2$ (25%) | 50° C. | 84.9 |
| 27 | 25% acetic | 84.5 mg | $H_2O_2$ (25%) | 50° C. | 3.5 |
| 28 | Glacial acetic acid | 84.1 mg | $H_2O_2$ (25%) | 50° C. | 100 |
| 29 | 25% acetic | 8.4 mg | $H_2O_2$ (50%) | 50° C. | 1.3 |
| 30 | Glacial acetic acid | 8.5 mg | $H_2O_2$ (50%) | 50° C. | 99.2 |
| 31 | 25% acetic | 83.7 mg | $H_2O_2$ (50%) | 50° C. | 2.7 |
| 32 | Glacial acetic acid | 83.5 mg | $H_2O_2$ (50%) | 50° C. | 100 |
| 33 | Glacial acetic acid | 84.0 mg | $H_2O_2$ (50%) | 50° C. | 100 |
| 34 | 25% acetic | 8.6 mg | $H_2O_2$ (50%) | RT | 0 |
| 35 | Glacial acetic acid | 8.6 mg | $H_2O_2$ (25%) | RT | 11.6 |
| 36 | 25% acetic | 84.6 mg | $H_2O_2$ (25%) | RT | 0 |
| 37 | Glacial acetic acid | 84.4 mg | $H_2O_2$ (25%) | RT | 92.9 |
| 38 | 25% acetic | 8.4 mg | $H_2O_2$ (25%) | RT | 0 |
| 39 | Glacial acetic acid | 8.4 mg | $H_2O_2$ (50%) | RT | 21 |
| 40 | 25% acetic | 84.3 mg | $H_2O_2$ (50%) | RT | 0.5 |
| 41 | Glacial acetic acid | 84.7 mg | $H_2O_2$ (50%) | RT | 95.9 |

Example 42

Quantitative oxidation of DBT is noted when employing 6 mole equivalents of NaOCl in place of $H_2O_2$ as the oxidant according to the conditions of Example 22.

One Possible Embodiment of the Oxidant Utilization Selectivity

The hydrogen peroxide content of each phase was determined by titration with Ceric Sulfate, according to equation 1. After the titration endpoint had been reached, an excess of potassium iodide was added to the solution. The hydroiodic acid formed in acidic media reacts with peracetic acid to liberate iodine, according to equation 2. A standard solution of sodium thiosulfate was then used to titrate the liberated iodine, as shown in equation 3. The endpoint of this titration was used to calculate the peracetic acid content of each phase.

(1)

(2)

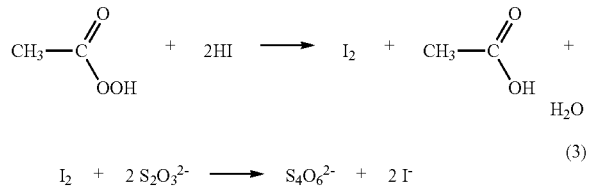
(3)

The titrations were performed manually using fresh, commercially available standardized reagents. The procedures were conducted quickly and at low temperature (0° C.) to prevent undesired degradations.

Oxidations

The oxidation experiment utilized straight-run diesel (1.7446% S) combined with three equivalents of glacial acetic acid in an open glass batch reactor. To this was added a measured aliquot of about 40% by weight solution of bis (glycerol)oxotitanium(IV)) in methanol followed by a measured quantity of the oxidant (50% $H_2O_2$, Aldrich) (5 mole equivalents: S). A heated circulating bath was used to control temperature (about ±0.1K) of the reactor (J-KEM), typically set at about 323 K (50° C.). The reaction was agitated at about 1000 rpm for about 1 hour with an overhead stirrer. A control reaction without Ti-catalyst was similarly run to quantify the autothermal degradation of hydrogen peroxide in the absence of the catalyst over the same time period.

Titrations

An exactly weighed amount of the sample phase was added to an Erlenmeyer flask containing about 2 ml of 5 N ice-cooled sulfuric acid, about 25 g of ice (crushed cubes) and about 3 drops of ferroin indicator solution.

The sample was titrated with about 0.1 N cerium(IV) sulfate until the appearance of the color changed from salmon to light blue (endpoint). The volume of cerium(IV) sulfate used (Vol 1) was recorded at the endpoint.

Then about 10 ml of a 20% potassium iodide solution was added to the titrated sample and diluted to approx. 300 ml with de-ionized water (brown color). This was then titrated with about 0.1 N sodium thiosulfate until the brown color became pale. A few drops of starch solution were added and the titration was continued until the solution turned from purple to salmon/pink. The final volume of sodium thiosulfate used was recorded as the endpoint.

The content of hydrogen peroxide in the sample (% wt) was calculated as follows:

% $H_2O_2$=mL Ce(IV)Sulfate×170.07/Sample Weight (mg)

The content of peracetic acid in the sample (% wt) was calculated as follows:

% PAA=mL thiosulfate×380.17/Sample Weight (mg)

The above procedure was repeated for each phase of the reaction (acetic acid phase and diesel phase) mixture in triplicate and the data was reported as the mean result.

Results

The oxidation experiments were intentionally conducted with the ratios shown in Table 1 for the purpose of fully demonstrating the unique selectivity demonstrated by the bis(glycerol)oxotitanium(IV) catalyst towards sulfoxidation.

TABLE 7

| Experimental Ratios | |
|---|---|
| Acetic Acid:Diesel (wt:wt) | 3:1 |
| $H_2O_2$:Sulfur (mole:mole) | 5:1 |
| Sulfur:Ti (mole:mole) | 20:1 |
| $H_2O_2$:Ti (mole:mole) | 100:1 |

The Ti-catalyzed experiments were compared to control experiments conducted without Ti catalyst. Analysis by GC-SCD (insert conditions) shows substantially no sulfur-bearing species in the diesel phase of the Ti-catalyzed run, while the control lacking Ti displayed very little S-compound removed and a small amount removed was most likely by extraction.

The concentration of peroxide and peracid in each phase is also informative with respect to the equilibrium distribution achieved in the batch system.

TABLE 8

Titration Results (moles) (Avg of 3 titrations)

| 1 Stream | 2 No Ti Dsl Control 1 hr | 3 Ti Decalin 1 hr† | 4 No Decalin 1 hr | 5 No catalyst Decalin 1 hr | 6 +ROH – Ti Decalin 1 hr | 7 Catalyst Diesel 1 hr | 8 Catalyst Diesel 12 min | 9 Catalyst Diesel 8 min |
|---|---|---|---|---|---|---|---|---|
| [Peroxide] In | 0.2724 | 0.2749 | 0.2723 | 0.2724 | 0.2732 | 0.2724 | 0.2723 | 0.2749 |
| [$H_2O_2$] Acetic phase | 0.2114 | 0.1994 | 0.2099 | 0.2441 | 0.2456 | 0.1125 | 0.1744 | 0.1861 |
| [Peracid] Acetic phase | 0.0111 | 0.0124 | 0.0097 | 0.0307 | 0.0287 | 0.0083 | 0.0056 | 0.0060 |
| [$H_2O_2$] Oil phase | 0.0011 | 0.0006 | N/A | 0.0006 | 0.0006 | 0.0005 | 0.0007 | 0.0007 |
| [Peracid] Oil phase | 0.0007 | 0.0002 | N/A | 0.0004 | 0.0004 | 0.0007 | 0.0003 | 0.0003 |
| Total [Oxidant] Left | 0.2243 | 0.2126 | 0.2196 | 0.2757 | 0.2752 | 0.1220 | 0.1810* | 0.1931* |
| [$H_2O_2$] to Sulfone @ 100% | N/A | N/A | N/A | 0.0000 | 0.0000 | 0.1090 | 0.0913* | 0.0818* |
| [Oxidant] Loss | 0.0481 | 0.0623 | 0.0527 | 0.0000 | 0.0000 | 0.0414 | 0.0000* | 0.0000* |

*Incomplete conversion (?); †Re-ran 2× extra to confirm (1st run in v1.1 sat through lunch)

The results in Table 8 clearly demonstrate that contact time may be a relevant parameter to oxidant selectivity. Peroxide loss may most likely occur via oxygen evolution since the same amount of oxidant loss occurs with or without an oil phase (Columns 3&4). Minimizing contact time appears to benefit selectivity (Columns 8&9). Interestingly, straight-run diesel shows substantial oxidant loss without Ti-catalyst (Column 2) in contrast to the decalin system without Ti-catalyst (Column 5). Straight-run diesel does contain metals capable of catalyzing the oxygen evolution reaction, and that may explain the aforementioned observation. In addition, direct oxidation of Sulfur-species according to FIG. 2 (Mercaptans, etc) in diesel presents another potential pathway for oxidant utilization in the absence of catalyst. Clearly, peroxide loss may be minimized by shortening contact time, decreasing oxidant concentration, and increasing Sulfur:Ti ratio (to enhance rate). The optimum run time to complete conversion and maximum selectivity under these conditions appears to be 20 minutes or less based upon model systems.

The oxidation experiments were conducted with the ratios shown in Table 9 for the purpose of fully demonstrating the unique selectivity demonstrated by the bis(glycerol)oxotitanium(IV) catalyst towards sulfoxidation.

TABLE 9

Experimental Ratios

| | |
|---|---|
| Acetic Acid:Decalin (wt:wt) | 5:1 |
| $H_2O_2$:Sulfur (mole:mole) | 2.4:1 |
| Sulfur:Ti (mole:mole) | 14:1 |
| $H_2O_2$:Ti (mole:mole) | 33.3:1 |
| Reaction Time | 20 min |

Dibenzo Thiophene (DBT) conversion was assayed by high-pressure liquid chromatography (HPLC) and oxidant selectivity was measured by titration. The results are tabulated in Table 10 below.

TABLE 10

| | |
|---|---|
| Moles Peroxide In | 0.0132 |
| Moles Oxidant Remaining (Titration) | 0.0023 |
| % Conversion to Sulfone (HPLC) | 99.5% |

TABLE 10-continued

| | |
|---|---|
| % Conversion (Titration) | 99.1% |
| Oxidant Selectivity | 99+% |

The oxidant selectivity in the model system above was greater than 99%.

CONCLUSION

In summary, the bis(glycerol)oxotitanium(IV) catalyzed oxidation of sulfur compounds in model diesel appears to possess very high oxidant selectivity to sulfone formation (99+%). Peroxide loss in straight-run diesel appears sensitive to contact time. As shown above, oxidant selectivity was at least greater than 99.0%.

Substrate Selectivity

Example 43

Figure 10:
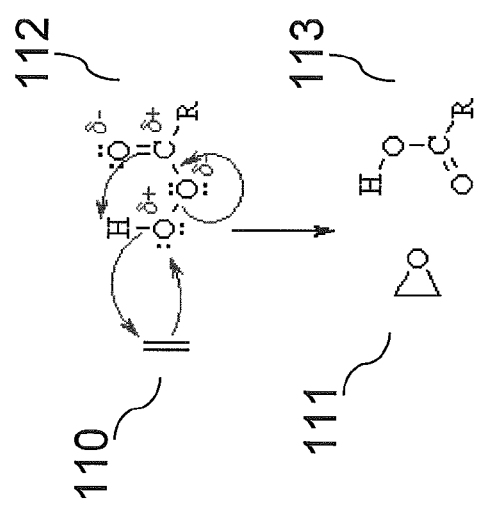
FIG. 10 is a graphic depiction of an indiscriminate reaction mechanism of olefins with peracids in accordance with prior sulfoxidation reagents.

One possible embodiment of an indiscriminate effect of prior art catalysts on olefins is graphically demonstrated by the mechanism shown in FIG. 10. To examine the selectivity towards olefin substrates using the catalyst of the present disclosure, experiments employing external, internal and mixed external and internal olefinic substrates were conducted.

Model oil was prepared by independently dissolving the olefin (styrene, trans-stilbene, and limonene) to 10% by weight in d8-toluene (6 grams). The oxidation experiments were carried out by combining acetic acid (18 g) with the model oil in a glass batch reactor, adding 100 µL of a 40% by weight solution of bis(glycerol)oxotitanium(IV) in methanol and then adding 5 mole equivalents of 50% $H_2O_2$ solution (olefin basis). A heated circulating bath was used to control temperature (±0.1K) of the reactor (J-KEM), typically set at 323 K (50° C.). The experiment was run for an hour with aliquots pulled at 15 minutes and 1 hour for conversion. After 15 minutes no oxidation was noted for either olefin by $^1$H- and $^{13}$C-nuclear magnetic resonance spectroscopic (NMR) analysis. After about 1 hour, no oxidation was observed for styrene and only partial epoxidation (13%) was noted for trans-stilbene during that period.

Model oil was prepared by dissolving carbazole (10%) in $d_8$-toluene (6 grams). The oxidation experiment was carried out by combining acetic acid (18 g) with the model oil in a glass batch reactor, adding 100 μL of a 40% by weight solution of bis(glycerol)oxotitanium(IV) in methanol and then adding 5 mole equivalents of 50% $H_2O_2$ solution (nitrogen basis). A heated circulating bath was used to control temperature (±0.1K) of the reactor (J-KEM), typically set at 323 K (50° C.). The experiment was run for an hour with aliquots pulled at 15 minutes and 1 hour for conversion. After 15 minutes complete oxidation was noted for carbazole as evidenced by disappearance of the N—H stretch by $^1$H-NMR. The catalyst appeared to oxidize aromatic amines.

Experiment 44

Examination of the effect of the catalytic process of the present disclosure on tertiary benzylic hydrocarbons was performed employing a variation of General Method A, replacing DBT by cumene according to the quantities shown in the table below. The reaction was examined by chromatographic techniques and compared to the results for all inputs against standards. No cumene oxidation products were observed. Specifically, in an oil stream that contains benzylic hydrocarbons, the catalyst of the present disclosure appears to not adversely affect the product contents in the oil stream. The catalyst of the present disclosure appears to be highly sulfur specific. In particular, if the oxidant were to adversely attack the hydrocarbons, then the quality of the fuel which was ultimately distilled would be reduced. Experiments 43 and 44 show that the catalytic process of the present disclosure does not significantly oxidize olefins, nor benzylic hydrocarbons, such results are considered to be new and unique with respect to the present disclosure.

TABLE 11

| Decalin Qty (g) | Acid Qty (g) | Catalyst Qty (μl) | Oxidizer Qty (g) | Temp (° C.) | Time |
|---|---|---|---|---|---|
| 12.01 | 24.0357 | 100 | 6.0451 | 50 | 5 |
| 12.01 | 24.0357 | 100 | 6.0451 | 50 | 10 |
| 12.01 | 24.0357 | 100 | 6.0451 | 50 | 15 |
| 12.01 | 24.0357 | 100 | 6.0451 | 50 | 20 |
| 12.01 | 24.0357 | 100 | 6.0451 | 50 | 30 |
| 12.01 | 24.0357 | 100 | 6.0451 | 50 | 45 |

Possible Embodiments of the Refinery Feed Experiments

Experiments were conducted on various sources of refinery feeds, such as Straight-Run Diesel (~2.12% S), Combined Gas-Oil (2.90% S), Vacuum Gas-Oil (3.25% S), and crude oil (6.05%). Acetic acid, catalyst, and oxidant were added according to the feeds. Reactions were carried out in glass vessels heated in water bath (45-55° C.) for varying times. Aliquots of the oil layer were taken during and after the reaction to be analyzed for sulfur content by using a XOS Sindie 7039 XRF x-ray fluorescence spectrometer. Some experiments included a complete separation of layers using a separation flask and BÜCHI Rotary evaporator.

TABLE 12

| Refinery Feed | Feed Qty (g) | Acetic Qty (g) | Peroxide Qty (g) | Final Sulfur |
|---|---|---|---|---|
| Straight Diesel | 30.015f | 90.1 | 6.79 | 13.6 ppm |
| Gas Oil | 25.992 | 75.04 | 8.64 | 1.02% |
| Comb. Gas Oil | 20.053 | 20.08 | 5.46 | 0.91% |
| Crude | 1.43 | 50.0 | 0.52 | 0.524% |

It has been confirmed through extensive experimentation that a solid titanyl sulfoxidation catalyst containing the bis (glycerol)oxotitanium(IV) composition described herein, when bound to a support surface (organic polymer or inorganic oxide) or within the backbone of a polymer, is effective to oxidize sulfur compounds from organic fluid streams. The resulting oxidized sulfur compounds may be substantially removed using commonly known separation techniques. Suitable oxidants may include, but are not limited to, $H_2O_2$, NaOCl, $O_2$, Air, mixtures thereof, and other suitable oxidants that readily react with the solid titanyl sulfoxidation catalyst to affect the desired sulfoxidation. Suitable phase transfer agent/solvents may include, but are not limited to, polar protic liquids such as acetic acid, formic acid, propanoic acid, and the like. Suitable organic fluid streams may include, but are not limited to, gasolines, diesels, jet oils, heavy oils, heavy sour crude oil, and other derived products typical of refinery products and intermediates. Suitable sulfur compound substrates may include, but are not limited to, alkyl- or aromatic-thiols, -sulfides, -sulfoxides, alkyl- or aromatic-thiophenes and other refractory sulfur-containing compounds.

The solid titanyl Sulfoxidation catalysts utilized in the experiments were heterogeneous variants of the catalyst described above. The temperatures employed were relatively mild (ambient to 90 C, typically less than 50 C). The solid titanyl sulfoxidation catalysts concentrations were usually less than 0.004.

There are many organosulfur compounds in petroleum products with typical molecular structures being illustrated in FIG. 2. Thiophenic (ring sulfur) compounds with alkyl substituents often boil significantly higher than the above parent compounds. Each carbon atom or methyl group R, R' increases boiling point by 20° to 40° F. (12° to 22° C.). Oxidation of the sulfur tends to substantially increase the boiling point, sometimes by several hundred degrees C., facilitating separation by thermal techniques. In addition, sulfoxidation substantially changes the polarity of the product facility separation by extraction. Thus, sulfoxidation provides several alternative means of removing unwanted sulfur compounds from sulfur containing hydrocarbon streams.

One Possible Embodiment of the Conventional Oxidation Mechanism

Figure 3:
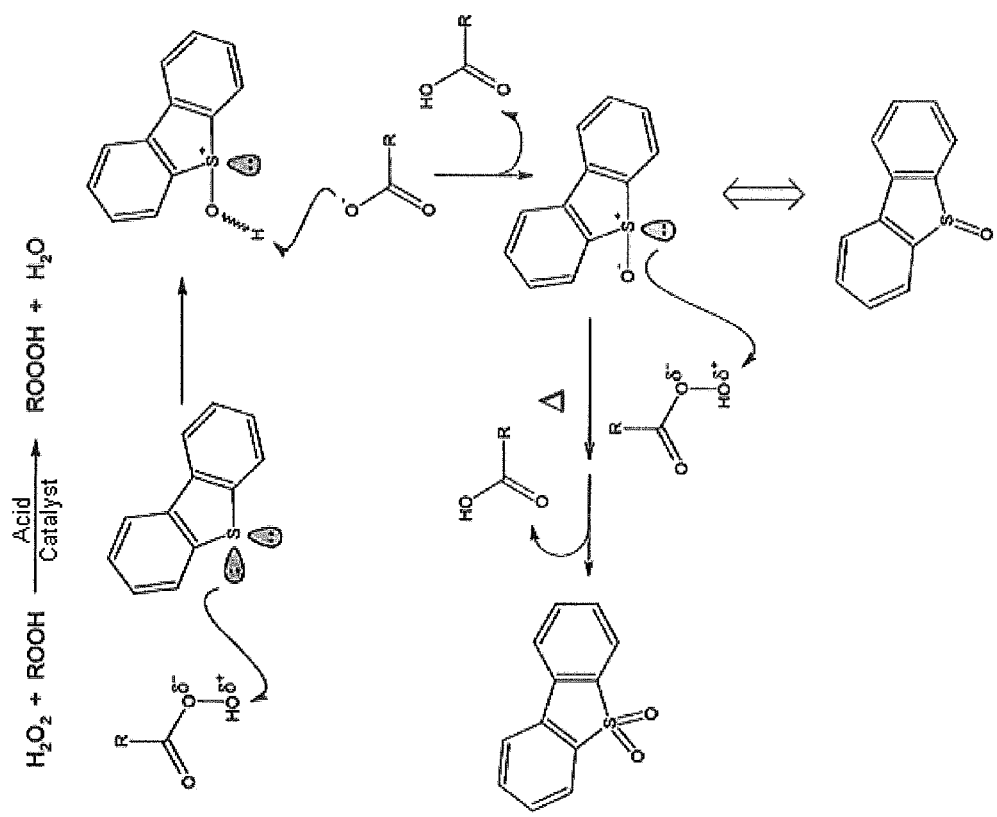
FIG. 3 is a graphic depiction of a prior conventional oxidation mechanism.

Conventional ODS theory describes sulfoxidation occurring initially to form sulfoxides and subsequently sulfoxides become sulfones via reaction with active oxygen in the form of a peracid generated in situ by interaction of an acid with an oxidant (i.e. hydrogen peroxide) in the presence of an acid catalyst (FIG. 3). The reaction conditions are relatively mild (atmospheric pressure, 95° to 212° F.). Typically, the reaction mixture consists of two phases; however, at temperatures greater than 50 C a single phase may result. Substantial extraction of sulfone occurs from the light phase (understood to have a density less than the heavy phase) into the heavy phase, reducing the net sulfur concentration in the hydrocarbon phase.

As illustrated in FIG. 3, the reaction includes a nucleophilic attack of the sulfur bond by a peracid reagent, which generates a hydroxy sulfur intermediate that undergoes a rearrangement to produce a traditional organic acid byproduct and a sulfoxide intermediate. The sulfoxide intermediate may further undergo the same chemical reactions, nucleophilic attack with another peracid reagent to produce a carboxylic acid byproduct and the end product sulfone. If the reaction stops at a first step and does not undergo a second chemical attack by a peracid reagent, the reaction may stop at a sulfur-oxide intermediate stage, as shown at the bottom of FIG. 3.

The above reaction, as illustrated in FIG. 3, was initially believed to be the operative chemical reaction mechanism. However, after undertaking a detailed chemical kinetics study varying the substitution groups at the four and six position of dibenzothiophene, an important discovery was made. The substitution patterns on the chemical structure suggest that the reaction mechanism involves the titanium center in the oxidation mechanism, as shown in the more detailed diagram, FIG. 4.

The kinetics experiments appeared to demonstrate that various sulfur compounds react with the catalyst at different rates. Referring now to the reaction mechanism illustrated in FIG. 4 and the Kinetics plot obtained employing general method G illustrated in FIG. 12, it is believed that a titanium species 50, such as, for example, bis(glycerol)oxotitanium (IV), and polymeric versions described herein, reacts with the sulfur compounds 52 and the like, to form an intermediate state 56. During this reaction, the oxygen atom attached to the titanium species 50 is transferred to the sulfur species 52 through a series of re-arrangement reaction steps at intermediate equilibrium state, 56. The chemical constitution of the sulfur compound 52 has a dramatic impact on how rapidly it interacts with the catalyst composition 50.

Figure 4:
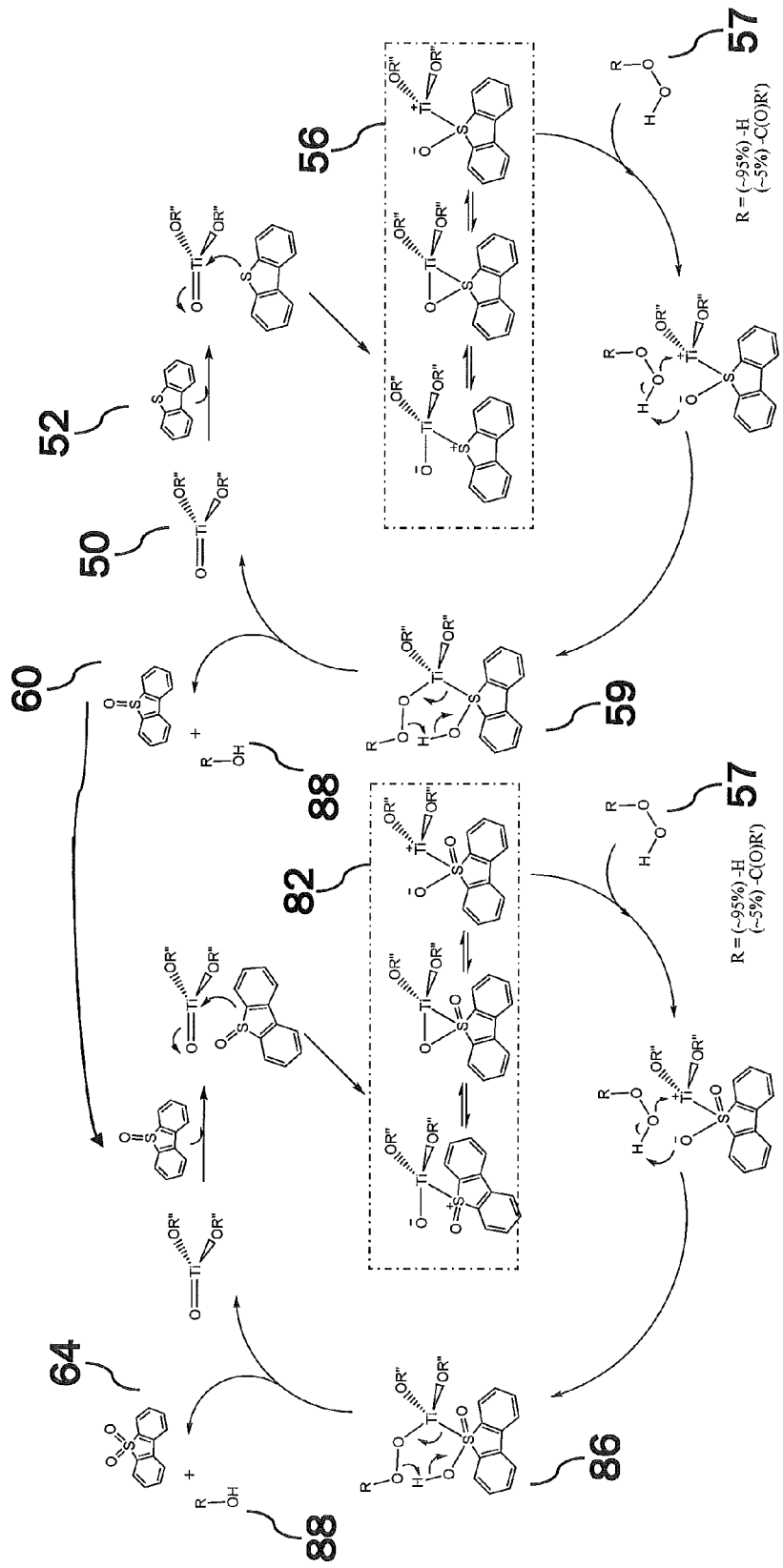
FIG. 4 is a graphic depiction of the Lewis acid catalyzed sulfoxidation mechanism according to the present disclosure.

As stated above, FIG. 4 illustrates the reaction mechanism that results in the formation of sulfoxide and ultimately toward the formation of the sulfone products 64. One feature of the catalyst is when the sulfur compound 52 approaches the titanium center, the sulfur compound competes for dative coordination on the titanium center prior to the sulfur compound reacting with titanium oxygen double bonded moiety to form the sulfur oxide intermediate. One feature of the catalyst is that it includes latently coordinated hydroxyl moieties from the ligands that stabilize the titanium oxidation state such that sulfur competes against the latently coordinated hydroxyls. It is presently believed that the selectivity of the catalyst is dictated by the strength of that hydroxyl to titanium coordination environment.

While not wishing to be bound by theory, it is presently believed that the most advantageous results of the present disclosure are achieved according to the reaction mechanism illustrated in FIG. 4.

It is presently believed that organosulfur oxidation occurs in two reaction steps. In the first step, the sulfur compound may irreversibly react with the catalyst and oxidant to form a sulfoxide. The sulfoxide may further be at with the catalyst and oxidant to form sulfur. The rate of formation of sulfoxide appears to be slower than the rate of formation of the sulfone of the same molecule.

The kinetics data of FIG. 12 using the catalyst of the present disclosure have shown that reactivity follows the order DBT>BT>MDBT>DMDBT. This relative trend substantially differs from that described by PetroStar and also by Qian where they observe that sulfone formation follows the trend: DMDBT>MDBT>NBT>DBT>BT using prior art catalysts. Indeed, the reaction extent and sulfoxidation selectivity seem to indicate that the catalysts plays a unique role in the reaction mechanism, as described graphically in FIG. 4.

In summary, FIG. 4 illustrates one representative example of a titanium species catalyst 50, such as, for example, bis(glycerol)oxotitanium(IV) or derivative solid titanium catalyst as described above in the present disclosure, that may be useful to remove sulphur species 52 and the like sulfur compounds, as defined in FIG. 2, from petroleum products. The titanium species catalyst 50 reacts with sulfur compounds to form an intermediate state 56. During this reaction, the oxygen atom attached to the titanium species catalyst 50 is transferred to the sulphur species 52 through a series of re-arrangement reaction steps at intermediate equilibrium state, 56, the oxidant is illustrated as entering the equilibrium state at 57 to form a new state at 58. The reaction continues through the state at 59 until the bond between the titanium species catalyst 50 and the sulphur species 52 and the byproduct species is broken resulting in the sulfoxide component 60 being freed or eliminated from being bound to the titanium species catalyst 50, regenerating titanium species catalyst 50.

The eliminated sulfoxide component 60 may then be recycled through the same exact reaction process cycle 62 and eventually has two oxygen atoms bound to the sulfoxide component 60, the second formed two oxygen atom sulfoxide component being illustrated at 64. Specifically, as shown on the left side of FIG. 4, the sulfoxide component 60 may react in the presence of the titanium species catalyst 50 and may generate the equilibrium transition state 82. That equilibrium transition state 82 may further react with another equivalent of oxidant 57 and may form an intermediate transition state 86. The intermediate transition state 86 may further rearrange, regenerating the titanium species catalyst 50 in the form of titanium species catalyst 50 and producing the byproduct sulfone 64 and the oxidant byproduct 88.

The oxygen atoms of the titanium species catalyst 50 may be continually regenerated in a continuous cycle by the oxidant through the mechanism described above. At this point, it is believed that any material capable of transferring oxygen to the titanium species catalyst that allows the chemistry described to occur in the reaction cycle may function as an oxidant.

Possible Embodiments of Heterogeneous Catalysts

Figure 5:
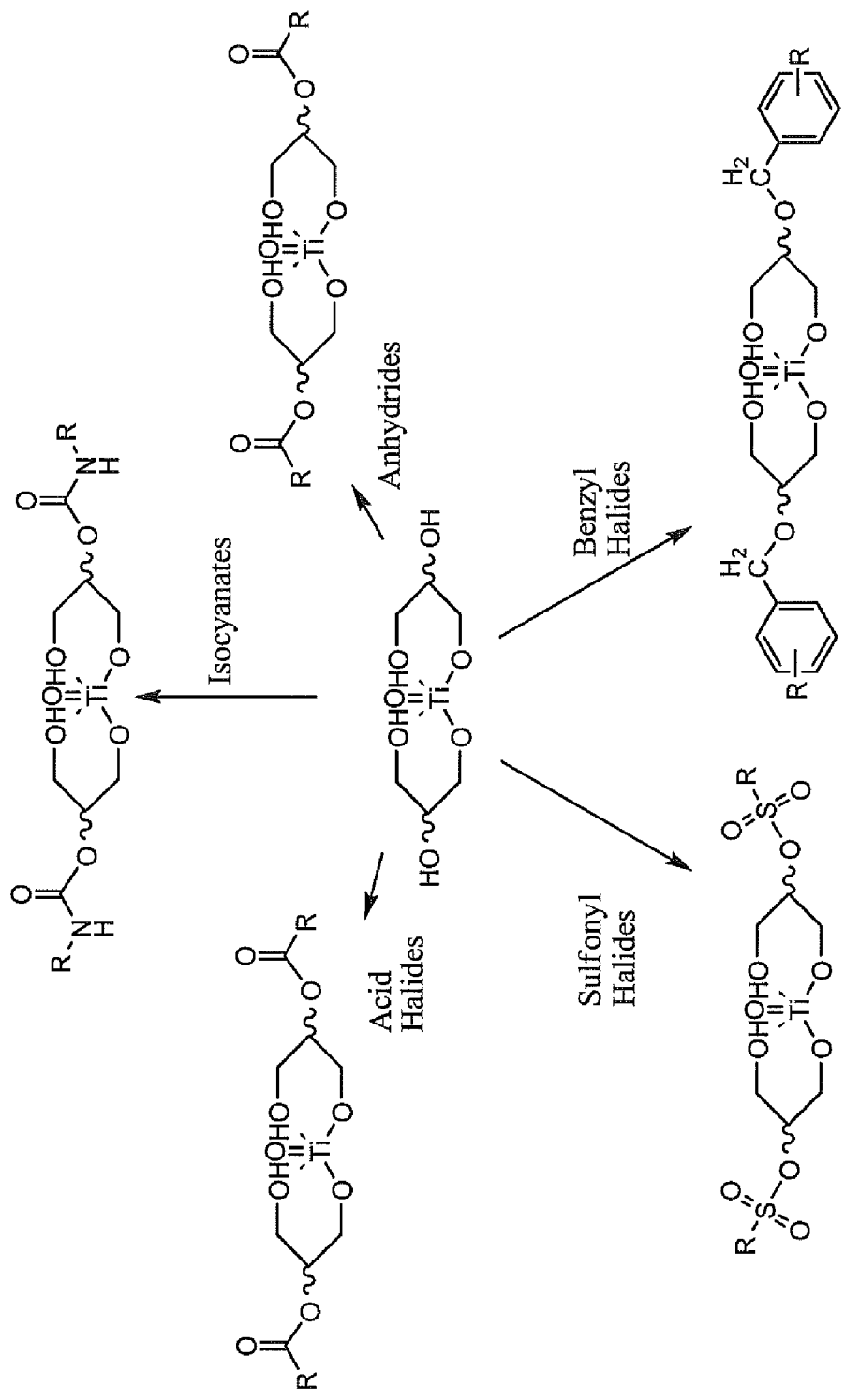
FIG. 5 is a graphic depiction of several representative chemical reactions that may occur on the hydroxyl groups of the catalyst of the present disclosure.

Titanyl catalysts bearing hydroxyl functionalities, that are not involved in chelation to the Ti center, are capable of undergoing reactions typical of free organic hydroxyl groups (FIG. 5).

The enabling power of this capability markedly distinguishes the bis(glycerol)oxotitanium(IV) composition catalyst from traditional titanate catalysts and compositions as demonstrated herein. The number of novel and unique compositions and enabling chemistries that can arise from the capability of bonding the catalyst to surfaces (FIG. 6A-D) or embedding it in the backbone of polymers and copolymers (FIGS. 7 and 9) by reaction with bi-functional monomers makes the bis(glycerol)oxotitanium(IV) catalyst a revolutionary advance in the chemistry of titanium.

FIG. 5 illustrates various types of reaction chemistries that may convert the soluble form of the catalyst to a polymer bound insoluble form of the catalyst. Basically, the reactions illustrate multiple modes of enabling novel and unique compositions containing the titanyl moiety.

FIGS. 6A 1-3 illustrates several possible embodiments of surface bound titanium catalysts. As illustrated, the PS circle represents a substantially polystyrene sphere that may be purchased commercially. The polystyrene sphere may be purchased bearing isocyanate, acid chloride, benzyl chloride and other reactive functional groups capable of chemically bonding to the hydroxyl moiety of the catalyst producing a surface bound catalyst product.

Figure 6:
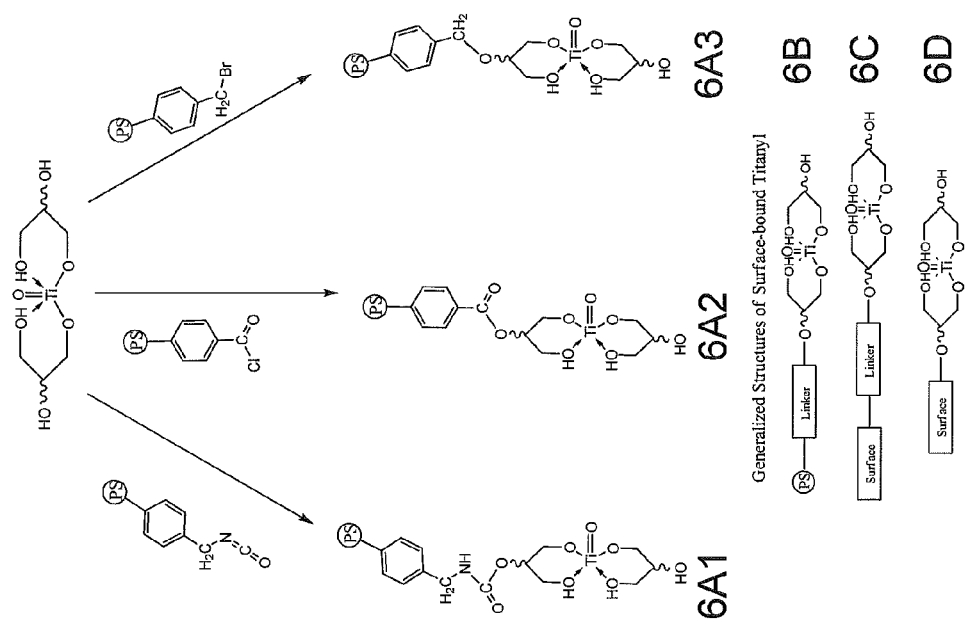

FIG. 6 also illustrates several surface bound catalytically active species in accordance with the present disclosure. One surface bound species illustrated is an isocyanate (6 A 1) functional polystyrene species that may react with the hydroxyl group of the catalyst to which may result in a surface bound catalytically active amide complex with the polystyrene bead. FIG. 6A2 illustrates the reaction of an acid halide functional polystyrene bead that may result in a surface bound catalytic active ester complex. FIG. 6A3 illustrates a benzylic halide surface bound species that may react with the hydroxyl group which may generate an ether-bound catalyst on the surface of a polystyrene bead.

FIGS. 6 B-C illustrate the utilization of a linker between the catalyst and the binding surface, with FIG. 6D illustrating the catalyst being bound directly to a surface.

Representative linkers are illustrated in FIG. 5 and may include, but are not limited to, isocyanates, acid halides, sulfonyl halides, benzyl halide and anhydrides and mixtures thereof.

Figure 7:
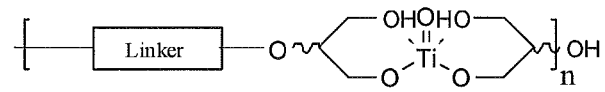
FIG. 7 is a graphic depiction of the generalized structure of a representative polymeric catalyst of the present disclosure, where the group defined as linker may be any chemical moiety which can react with the hydroxy functionalities of catalyst of the present disclosure, such that an alternating chain structure is formed thereby.

FIG. 7 illustrates a generalized structure of the polymeric catalyst of the present disclosure. The polymeric version of the catalyst contains a linking group. The linking group may be derived from a bi-functional chemical of the general formula, Q-R-Q' wherein Q and Q' are each independently chemical reactive groups that react with hydroxyl groups on the catalyst. Q and Q' may comprise, for example, isocyanates, anhydrides, sulfonyl halides, benzyl halides, carboxylic acid halides, phosphoryl acid halides, silyl chlorides, or any chemical functionality capable of reacting with the —OH pendant group of the catalyst. A further component of the linking group is denoted by R wherein R may comprise alkyl groups (including linear, branched, saturated, unsaturated, cyclic, and substituted alkyl groups, and wherein hetero atoms, such as oxygen, nitrogen, sulfur, silicon, phosphorus, and the like can be present in the alkyl group), typically with from 1 to about 22 carbon atoms, preferably with from 1 to about 12 carbon atoms, and more preferably with from 1 to about 7 carbon atoms, although the number of carbon atoms can be outside of these ranges, aryl groups (including substituted aryl groups), typically with from about 6 to about 30 carbon atoms, preferably with from about 6 to about 15 carbon atoms, and more preferably with from about 6 to about 12 carbon atoms, although the number of carbon atoms can be outside of these ranges, arylalkyl groups (including substituted arylalkyl groups), typically with from about 7 to about 30 carbon atoms, preferably with from about 7 to about 15 carbon atoms, and more preferably with from about 7 to about 12 carbon atoms, although the number of carbon atoms can be outside of these ranges, such as benzyl or the like, alkylaryl groups (including substituted alkylaryl groups), typically with from about 7 to about 30 carbon atoms, preferably with from about 7 to about 15 carbon atoms, and more preferably with from about 7 to about 12 carbon atoms, although the number of carbon atoms can be outside of these ranges, alkoxy groups (including substituted alkoxy groups, and wherein hetero atoms, such as oxygen, nitrogen, sulfur, silicon, phosphorus, and the like can be present in the alkoxy group), typically with from 1 to about 22 carbon atoms, preferably with from 1 to about 12 carbon atoms, and more preferably with from 1 to about 7 carbon atoms, although the number of carbon atoms can be outside of these ranges, polyalkyleneoxy groups (including substituted polyalkyleneoxy groups), such as polyethyleneoxy groups, polypropyleneoxy groups, polybutyleneoxy groups, and the like, typically with from about 3 to about 60 repeat alkyleneoxy units, preferably with from about 3 to about 30 repeat alkyleneoxy units, and more preferably with from about 3 to about 20 repeat alkyleneoxy units, although the number of repeat alkyleneoxy units can be outside of these ranges. The result of reacting the linking group and the catalyst produces a heterogeneous catalyst that may be described as an AB type copolymer. If more than one type of linking group was employed, according to the present disclosure, the polymer catalyst produced may be described more generically as a co-polymer.

Figure 8:
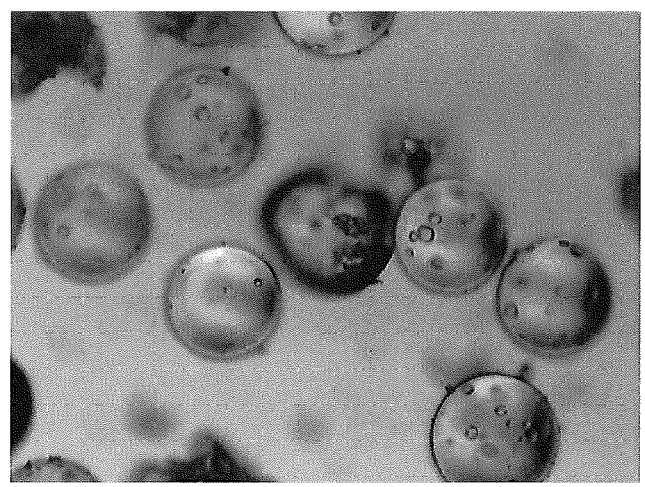
FIG. 8 is a photograph of a polystyrene isocyanate functionalized catalyst that shows the titanium chemical species reacted onto the surface of polystyrene spheres according to the present disclosure.

FIG. 8 is a photograph of a specific embodiment of the polystyrene bound catalyst described in FIG. 6 and also represents, in a generalized example, the types of surface bound and pore bound examples described in FIGS. 6B-D.

Figure 9:
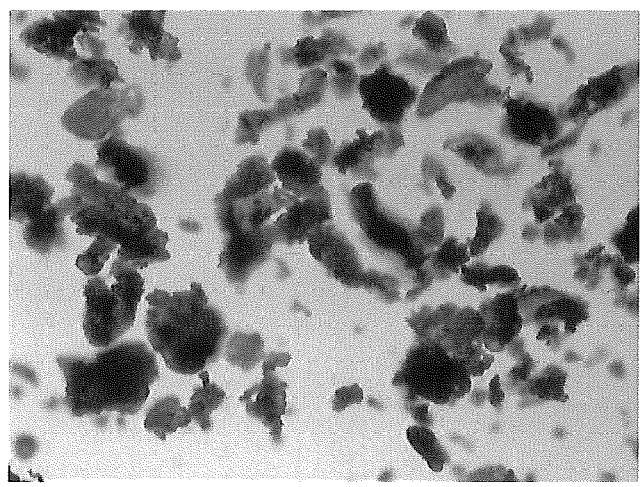
FIG. 9 is a photograph of one possible variant of the catalyst integrated within a polymeric support according to FIG. 7.

FIG. 9 illustrates another generalized structure of the polymeric catalyst of the present disclosure. FIG. 9 is a photograph of a particular polymeric catalyst of the present disclosure illustrating specific polymeric catalyst integrating with a bi-functional linker moiety, producing a highly cross-linked, solid polymeric catalyst, according to the present disclosure.

The following examples are the result of extensive experimentation evaluating the performance attributes of the heterogeneous variant of the bis(glycerol)oxotitanium(IV) of the present disclosure. As the result of our extensive experimentation to date, we believe the sulfoxidation catalytic process integrating the catalytic composition of the present disclosure represents a cost effective, safe, reliable, and highly efficient method to reduce sulfur levels in transportation fuels.

Possible Embodiments of Heterogeneous Catalysts Preparation

Experiments were conducted according to General Method H, as defined below. In some cases the catalyst from one experiment was washed, filtered, and re-used in further experiments.

General Method H

Pyromellitic dianhydride (PMDA, 2.18 g, 0.01 moles) was suspended in 20 ml of acetonitrile (or optionally DMSO depending upon solubility of PMDA and/or catalyst) in a 100 ml glass bottle containing a magnetic stir bar spinning at a rate to sufficiently mix the components. Bis(glycerol)oxotitanium (IV) (2.58 g, 0.0105 moles) was added with vigorous mixing at 80° C. The reaction continued for 4 hrs. After cooling the reaction mixture to room temperature, stirring was continued for an additional hour. The contents were poured very slowly into 150 ml of acetone giving rise to a white precipitate. The collected solids were dried in a vacuum oven overnight (22° C.). Yield was greater than 90%.

Example 45

3,3',4,4'-Benzophenone tetracarboxylic dianhydride (BTDA, 3.22 g, 0.01 moles) was reacted with bis(glycerol)oxotitanium(IV) (2.58 g, 0.0105 moles) according to the procedures in General Method H. Yield was greater than 90%.

Example 46

4,4'-Bisphenol A dianhydride (BPADA, 5.20 g, 0.01 moles) was reacted with bis(glycerol)oxotitanium(IV) (2.58 g, 0.0105 moles) according to the procedures in General Method H above. A yield of greater than 90% was obtained.

Example 47

5-(2,5'-Dioxotetrahydrol)-3-methyl-3-cyclohexene-1,2-dicarboxylic anhydride (B-4400, 2.64 g, 0.01 moles) was reacted with bis(glycerol)oxotitanium(IV) (2.58 g, 0.0105 moles) according to the procedures in General Method H. A yield of greater than 90% was obtained.

Example 48

Ethylene glycol bis(trimellitic anhydride) (TMEG-200, 4.10, 0.01 moles) was reacted with bis(glycerol)oxotitanium (IV) (2.58 g, 0.0105 moles) according to the methods of General Method H. A yield of greater than 90% was obtained.

FIG. 7 illustrates the generic products of the reactions above and FIG. 9 represents the catalyst prepared above in example 46. The examples described above employ telechelic anhydrides which are further capable of cross-linking. The resulting solid catalytic polymer material was further employed for sulfoxidation catalysis according to the systems and methods of the present disclosure.

Figure 11:
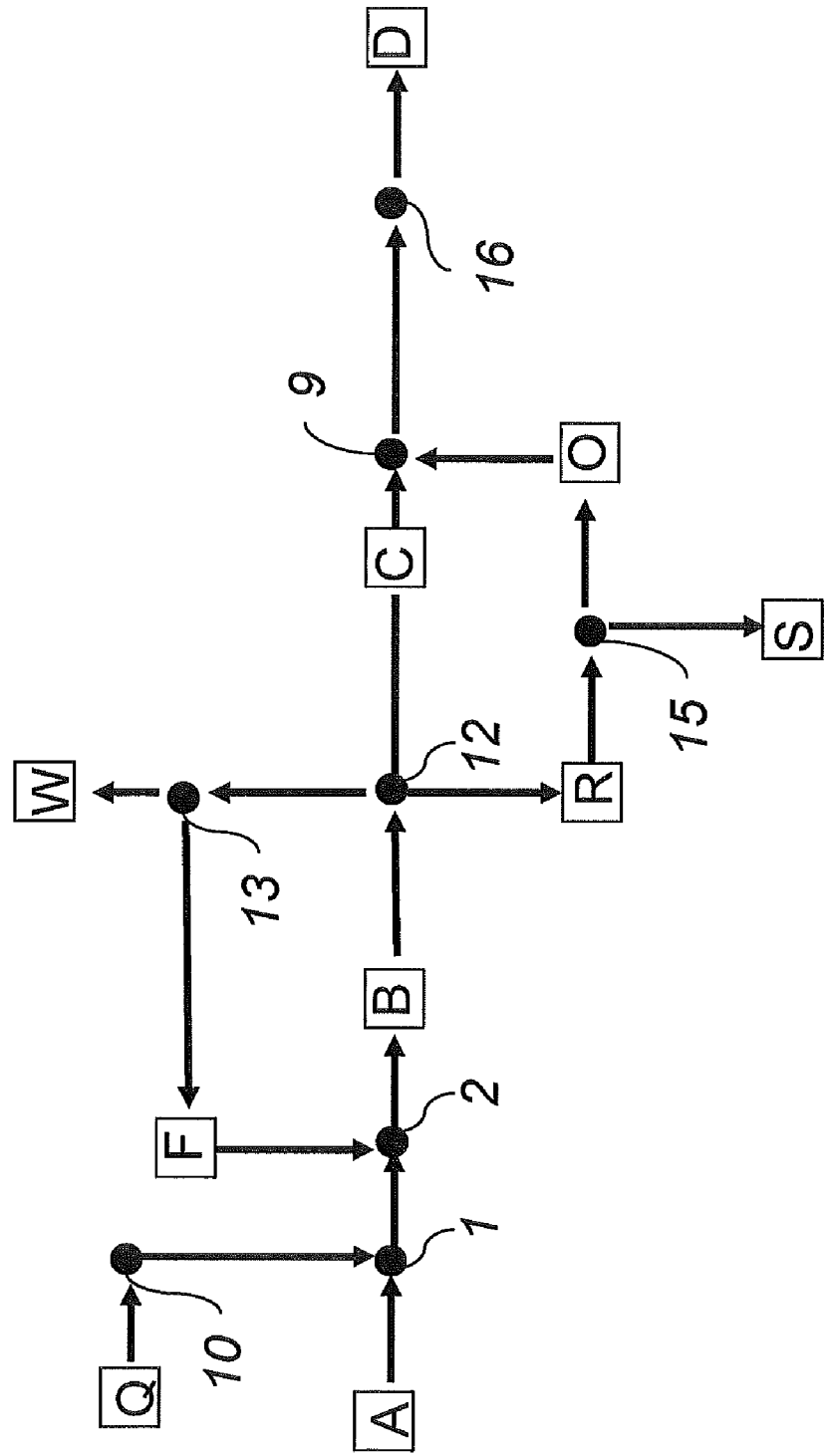
FIG. 11 is a process flow diagram of an alternative embodiment of a sulfoxidation process in accordance with embodiments of the present disclosure.

FIG. 11 is a process flow diagram of another embodiment of a system and process for sulfoxidation of a sulfur-rich hydrocarbon fluid employing catalysts such as described above. Source A may comprise a sulfur-rich hydrocarbon fluid stream input into the system at mixing point 1, where the hydrocarbon fluid stream may be a fluid such as those described above in paragraph 50. Source Q may comprise an oxidant introduced into the system at injection point 10, where the oxidant may comprise oxidants described above in paragraph 53, where the oxidant mixes with the hydrocarbon fluid stream at mixing point 1 to form a mixture. Source Q may comprise an electric input such that the oxidant is produced by electrolysis or source Q may comprise an oxidant production plant that delivers the oxidant by way of source Q.

The mixture from mixing point 1 may be combined with a polar protic fluid stream F and a catalyst in reactor 2 to form a reaction mixture, resulting in the sulfoxidation of sulfur-rich organic fluid within reactor 2. The catalyst may be those described above in paragraph 48. Reactor 2 may be a fixed bed reactor, a static mixer with a fixed bed reactor, a continuously stirred reactor, or any other known reactor capable of performing catalytic reactions with reaction mixtures.

A biphasic product mixture stream B may result from the reaction in reactor 2 and may be transferred from reactor 2 to separator 12, where an essentially sulfur-free hydrocarbon product stream C may be separated from a sulfur-rich hydrocarbon stream R and a wet polar protic fluid stream F resulting from the separation at separator 12. The wet polar protic fluid stream F is dried in dryer 13 (producing water stream W) before being recycled to reactor 2.

Sulfur-rich hydrocarbon stream R is heated in reactor 15 to produce essentially sulfur-free organic stream O and sulfur-enriched coke stream S. Essentially sulfur-free hydrocarbon streams C and O are combined at mixing point 9 and the resulting combination is separated into substantially sulfur-free, olefin rich hydrocarbon product streams D.

In some embodiments of the sulfoxidation systems and methods according to the present disclosure the mixing point/reactor/injection point may be combined into a single component which provides a sulfur-rich hydrocarbon fluid stream which is delivered to at least a first combination mixing point/reactor/injection point. An oxidant may be provided with the oxidant being delivered to the at least a first combination mixing point/reactor/injection point wherein the oxidant may be mixed with the hydrocarbon fluid stream at the at least a first combination mixing point/reactor/injection point to produce a mixture. A polar protic fluid stream and a catalyst are provided and the mixture may be combined with the polar protic fluid stream in the presence of the catalyst to form a reaction mixture, the combination resulting in the sulfoxidation of the sulfur-rich organic fluid within the at least first mixing point/reactor/injection point. The mixture stream from the at least a first combination mixing point/reactor/injection point id delivered to a first combination separator/dryer where the mixture stream may be separated from an at least a first substantially sulfur-free hydrocarbon product stream from a sulfur-rich hydrocarbon stream and the wet polar protic fluid stream. The wet polar protic fluid stream in the first combination separator/dryer may be dried and the dried polar protic fluid stream returned to the at least first mixing point/reactor/injection point. The sulfur-rich hydrocarbon stream may be transferred to a second reactor the sulfur rich hydrocarbon stream may be heated in the second reactor, the heating resulting in at least a second substantially sulfur-free organic stream and a sulfur-enriched coke stream. The two substantially sulfur-free streams may be transferred to the first combination mixing point/separator where the resulting combination may be separated into a substantially sulfur-free, olefin rich hydrocarbon product stream.

In some embodiments, the first combination mixing point/reactor/injection point may comprise separate components for the mixing point, the reactor and the injection point.

In other embodiments, the first combination mixing point/reactor/injection point may comprise separate components for the mixing point and a combination reactor/injection point.

In still other embodiments, the first combination mixing point/reactor/injection point may comprise separate components for the reactor and a combination mixing point/injection point.

In some embodiments, the first combination mixing point/reactor/injection point may comprise separate components for the injection point and a combination mixing point/reactor.

In other embodiments, the first combination mixing point/reactor/injection point may comprise separate components for each of the injection point, the mixing point and the reactor.

In still other embodiments, the first combination separator/dryer may comprise separate components for each of the separator and the dryer.

In some embodiments, a first combination mixing point/separator may comprise separate components for each of the mixing point and the separator.

In view of the foregoing, it should be evident that the globally recognized need to reduce sulfur levels in hydrocarbon streams such as gasoline and diesel fuels has been successfully addressed utilizing the catalysts of the present disclosure. Further, it should also be evident from the foregoing that the need for systems and processes that will have a minimal effect on the olefin content of such fuels so as to maintain the octane number (both research and motor octane number) has successfully been addressed utilizing the catalysts of the present disclosure.

Even further, the experimental data to date with respect to the systems and methods of the present disclosure indicates that the need to avoid the loss of the aromatic content of the cracked gasoline through saturation has been successfully addressed. Even the need for systems and processes that achieve desulfurization and maintain the octane number has been achieved utilizing the teachings of the present disclosure.

According to the teachings of the present disclosure, the need for a desulfurization systems and processes that function without a significant consumption of hydrogen so as to provide a more economical process for the treatment of cracked gasolines and diesel fuels has also been achieved by the teaching of the present disclosure as compared to systems and processes known to the inventors of the present disclosure at the time of development.

What is claimed is:

1. A sulfoxidation method comprising:
providing a hydrocarbon stream including at least one sulfur compound;
providing an oxidant;
providing a catalyst comprising a metal compound represented by the general formula $M_mO_m(OR)_n$, wherein M is a metal complex; R is carbon group having at least 3 carbon atoms, where at each occurrence R is individually a substituted alkyl group containing at least one OH group, a substituted cycloalkyl group containing at least one OH group, a substituted cycloalkylalkyl group containing at least one OH group, a substituted heterocyclyl group containing at least one OH group, or a heterocyclylalkyl containing at least one OH group; and the subscripts m and n are each independently integers between about 1 and about 8; and
contacting the hydrocarbon stream with the oxidant in the presence of the catalyst, resulting in the oxidation of the at least one sulfur compound.

2. The method of claim 1 further comprising:
providing a phase transfer agent/solvent.

3. The method of claim 2 wherein the phase transfer agent/solvent is selected from the group consisting of acetic acid, formic acid, propanoic acid, octenoic acid, butenoic acid, long chain aliphatic acids, alkyl substituted aromatic acids, other polar protic liquids, and mixtures thereof.

4. The method of claim 1 wherein the catalyst comprises: bis(polyol)oxotitanium(IV).

5. The method of claim 4 wherein the polyol further comprises:
ethylene glycol, glycerol, erythritol, sorbitol, xylitol, pentaerythritol, a sugar, a carbohydrate, and/or mixtures thereof.

6. The method of claim 1 wherein the method is carried out between 20 degrees Celsius and 90 degrees Celsius.

7. The method of claim 1 wherein the concentration of the catalyst is between 100.00% and 0.00004% by weight with respect to elemental sulfur.

8. The method of claim 1 wherein the catalyst is at least one of incorporated within a polymer and bound to a support surface, wherein the support surface comprises an organic polymer, an inorganic oxide, or mixtures thereof.

9. The method of claim 8 wherein the inorganic oxide is selected from the group consisting of:
silicates, aluminates, titanates, independently and/or mixtures thereof, and
wherein the organic polymer is selected from the group consisting of: polystyrene-co-divinylbenzene, containing reactive chemical functionalities comprising, isocyanates, anhydrides, sulfonyl halides, benzyl halides, carboxylic acid halides, phosphoryl acid halides, silyl chlorides, or any chemical functionality capable of reacting with the —OH pendant group of the catalyst.

10. The method of claim 1 wherein the catalyst is a solid in a form selected from the group consisting of a polymer, a complex, a cluster complex, a mixture of isomers, a nano-dimensional material, and mixtures thereof;
wherein the hydrocarbon stream including at least one sulfur compound is selected from a group consisting of gasoline, diesel fuel, jet oil, heavy oil, heavy sour crude oil, other refinery products and intermediates, and mixtures thereof, and
wherein the oxidant is selected from the group consisting of hydrogen peroxide, sodium hypochlorite, oxygen, trioxygen, air, permanganate compounds, nitrous oxide, and mixtures thereof and different forms thereof.

* * * * *